(12) United States Patent
Herrick et al.

(10) Patent No.: US 11,123,497 B2
(45) Date of Patent: *Sep. 21, 2021

(54) GAS REMOVAL APPARATUS AND RELATED METHODS

(71) Applicants: Norton Herrick, Boca Raton, FL (US); David Saloff, Pacific Palisades, CA (US); Richard Green, Santa Monica, CA (US)

(72) Inventors: Norton Herrick, Boca Raton, FL (US); David Saloff, Pacific Palisades, CA (US); Richard Green, Santa Monica, CA (US)

(73) Assignee: AILNH, LLC, Boca Raton, FL (US)

( * ) Notice: Subject to any disclaimer, the term of this patent is extended or adjusted under 35 U.S.C. 154(b) by 66 days.

This patent is subject to a terminal disclaimer.

(21) Appl. No.: 16/258,444

(22) Filed: Jan. 25, 2019

(65) Prior Publication Data
US 2019/0151570 A1    May 23, 2019

Related U.S. Application Data

(63) Continuation-in-part of application No. 16/132,961, filed on Sep. 17, 2018, now Pat. No. 10,874,806, which is a continuation-in-part of application No. 15/950,002, filed on Apr. 10, 2018, now Pat. No. 10,874,805, which is a continuation-in-part of application No. 15/116,998, filed as application No. PCT/US2014/016595 on Feb. 14, 2014, now Pat. No. 10,220,161.

(51) Int. Cl.
| | |
|---|---|
| *A61M 5/36* | (2006.01) |
| *A61M 5/142* | (2006.01) |
| *A61M 5/168* | (2006.01) |
| *A61M 5/14* | (2006.01) |

(52) U.S. Cl.
CPC .............. *A61M 5/36* (2013.01); *A61M 5/14* (2013.01); *A61M 5/142* (2013.01); *A61M 5/16822* (2013.01); *A61M 2205/18* (2013.01)

(58) Field of Classification Search
CPC ..... A61M 5/36; A61M 5/1411; A61M 1/3627
See application file for complete search history.

(56) References Cited

U.S. PATENT DOCUMENTS

| | | | | |
|---|---|---|---|---|
| 2,597,699 A | * | 5/1952 | Bauer | A61M 5/36 604/122 |
| 3,677,248 A | * | 7/1972 | McPhee | A61M 3/0241 604/500 |
| 3,778,973 A | * | 12/1973 | Martinez | A61M 1/3627 96/155 |
| 4,596,557 A | * | 6/1986 | Pexa | A61M 5/36 604/284 |

(Continued)

*Primary Examiner* — Laura A Bouchelle
(74) *Attorney, Agent, or Firm* — Steve Hassid; Partners Law Group, Inc.

(57) ABSTRACT

An apparatus having an outer wall that encompasses an interior chamber that holds a predetermined volume of fluid and gas where the gas rises to one end of the interior chamber and the fluid flows to the other end of the interior chamber. The apparatus also has an inlet port that allows for fluid to ingress into the interior chamber and an outlet port that allows for fluid to egress out of the interior chamber.

16 Claims, 14 Drawing Sheets

(56) References Cited

U.S. PATENT DOCUMENTS

| | | | | |
|---|---|---|---|---|
| 4,900,308 A | * | 2/1990 | Verkaart | A61M 5/36 |
| | | | | 604/126 |
| D328,788 S | * | 8/1992 | Sagae | D24/129 |
| 5,242,432 A | * | 9/1993 | DeFrank | A61M 39/26 |
| | | | | 604/247 |
| 2006/0189946 A1 | * | 8/2006 | Adams | A61M 5/36 |
| | | | | 604/251 |

\* cited by examiner

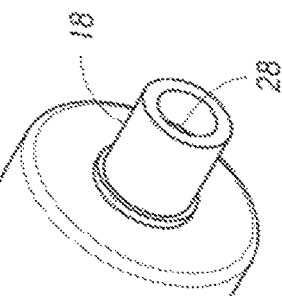
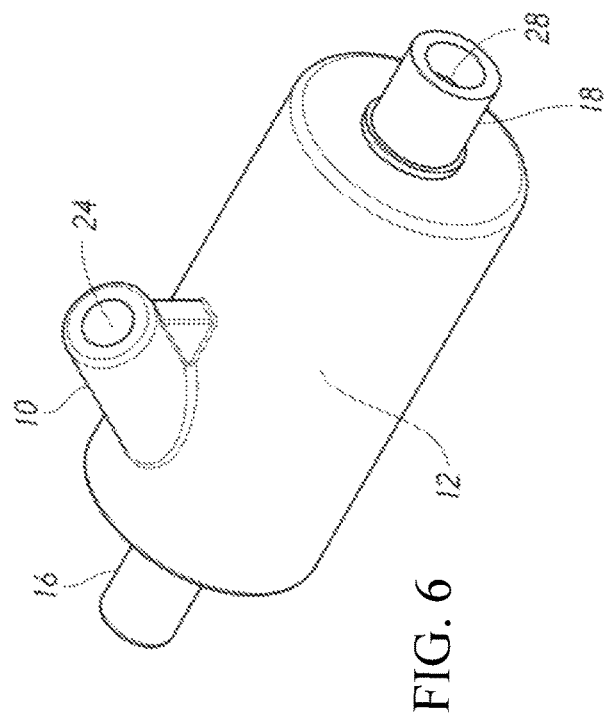
FIG. 6
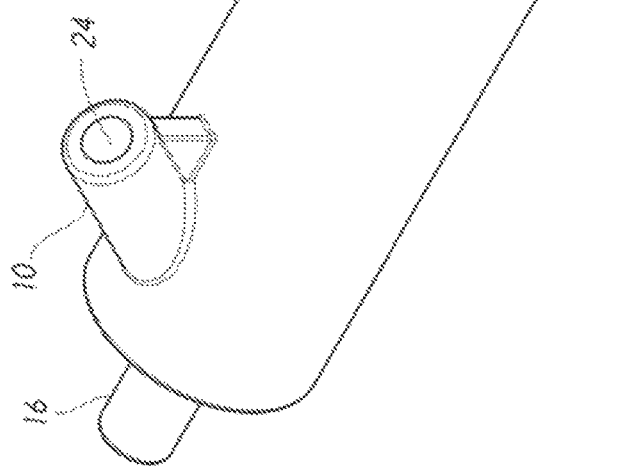
FIG. 7

GAS REMOVAL APPARATUS AND RELATED METHODS

CLAIM OF BENEFIT TO PRIOR APPLICATIONS

This application is a continuation-in-part application of U.S. patent application Ser. No. 16/132,961 filed on Sep. 17, 2018, which is a continuation-in-part application of U.S. patent application Ser. No. 15/950,002 filed on Apr. 10, 2018, which is a continuation-in-part of U.S. patent application Ser. No. 15/116,998 filed on Aug. 5, 2016, now published as U.S. Patent Publication 20170165435A1, which is a national filing of PCT/US2014/016595 filed on Feb. 14, 2014, all of which are incorporated herein by reference in their entirety.

FIELD OF THE DISCLOSURE

The present disclosure is related generally to the field of fluid delivery apparatuses and more particularly to apparatuses for removing unwanted gas (e.g., air) from a fluid, apparatus or device in a variety of industries and environments.

GENERAL BACKGROUND

Gas found in lines, such as intravenous fluid lines, hydraulic lines, water lines or pipes, or car fluid systems such as oil and brakes, often times forms air pockets which can be detrimental to the instrument or process. In the medical field, air in an intravenous fluid (IV) line can be deadly, so it would be vitally important to remove all air in an IV line. Another field includes an industrial system and hydraulic lines where air could slow down or cause damage to the equipment or product being produced. Problems associated with gas (often air) entering into a line is a problem that exists in various industries and services, including but not limited to, medical, research, laboratories, manufacturing, avionics, colonics, chemotherapy, and any other field or purpose where the introduction of a gas creates issues, problems, or negatively effects outcome of the process or product.

In the field of colonics, removing or preventing air bubbles from entering the user of the colonic systems is essential to a positive experience and to avoid potential problems caused by the introduction of air in the line of the colonic device.

Additionally, the inventions of the present disclosure can be used in a variety of industries and uses. For example and not by way of limitation, the inventions of present disclosure can be used in the beverage industry to, as an example, remove unwanted gas from the production of beverages (e.g., beer and soda).

Additionally, when drugs that are expensive, difficult to obtain or require special handling and require a precise dosage (e.g., drugs used for chemotherapy), the present inventions avoid having to discard and replace valuable drugs because the line must be purged/primed to remove the air bubbles. Further, in current technologies and devices, liquid frequently gets trapped in the devices when the bag is empty. There exists a need to have a device that does not have liquid in the device when the bag and tubing are empty. The inventions of the present disclosure provide this and other benefits indicated herein.

In the medical field, an air or gas embolism can occur when an air or gas bubble or embolus becomes trapped in a blood vessel or in the heart and obstructs the normal flow of blood through the blood vessel (e.g., a vascular air embolus (VAE)) or the heart. Air in a patient's veins can travel to the right side of the heart and from the heart to the lungs. Air trapped in vessels providing blood to the lungs can inhibit pulmonary circulation and cause chest pain and rapid breathing. In some patients, the air may pass to the left side of the heart and on to the brain or the coronary arteries, which can lead to more serious complications. The effect of an air embolism is directly related to the size of the embolus and the rate of entry of the air into the blood vessel. A 50 ml of air can cause hypotension and dysrhythmias, while a 300 ml of air can cause death if introduced rapidly. Generally, this occurs due to circulatory obstruction and cardiovascular collapse.

Air can be introduced into the blood vessels during surgery or other medical procedures, such as using a syringe. Air may be introduced in the form of bubbles trapped in a fluid introduced into the blood vessel (e.g., a blood transfusion, an IV fluid line supplying a fluid such as a saline solution or medicine). Additional air bubbles may be formed, for example, when priming the IV line if a roller clamp is released too quickly during the priming of the line. Small air bubbles may be present in the fluid as supplied.

The symptoms and clinical signs of air embolism are related to the degree of air entry into the circulation system. It is generally accepted that any amount of air that might enter the patient must be considered critical. The impact is directly correlated with the patient's condition, the volume of air, and the rate of accumulation. According to the Center for Medicare/Medicaid Services ("CMS"), air embolisms are on a very short list of events that can have immediately dire consequences and for which the body has zero tolerance.

One published article states that mortality amongst patients who suffered from an air embolism was 21%. More than one in five. (See McCarthy C J, Behravesh S, Naidu S G, Oklu R. *Air Embolism: Diagnosis, Clinical Management and Outcomes*. Kjaer A, ed. *Diagnostics*. 2017; 7(1):5. doi: 10.3390/diagnostics7010005.) Where an embolism doesn't lead to death, non-fatal episodes of venous air embolism lead to extensive diagnostic and therapeutic intervention by medical professionals. Thus, by conducting a cost evaluation of the risk done by assigning costs to their related clinical treatment and resulting extended length of stay, preventing the entrance of air into the patient's circulatory system can result in tangible budget savings for the healthcare provider. In the case of severe multiple complications, which require full ICU treatment, a hospital would have significant saving. Further, litigation costs and expenses can be in the millions of dollars as CMS has designated air embolisms as a "Never Event"—a serious and costly error in the provision of health care services that should never happen, and because of the designation as a "Never Event," the hospital or other provider must bear the responsibility and cost.

Various efforts have been made to try to prevent air from being introduced into the blood of a patient. Many of them require the use of complicated devices that attempt to solve the problem by having one or more sensors that detect air and cause an alarm to go off if air is detected in the line. While the alarms can be helpful, it does not solve the problem of preventing air from being introduced into the system or patient and creates other problems, some of which are discussed below. Other solutions to preventing air bubbles from being introduced into the blood often involve complicated devices that often are not completely successful and have components that wear out over time. Other solutions to preventing air bubbles do not function correctly if the amount of air or turbulence in the line is greater than expected. These and other solutions sometimes also include a system to detect when air is in the IV line. If an air bubble reaches the pump, an alarm may sound to alert a caregiver and the pump may turn off. The caregiver must then go to the patient and attempt to remove the air bubbles from the IV line. This practice consumes valuable time for the caregiver, increases costs associated with successful care giving, and, often times, creates an alarm fatigue for the caregiver, which is a serious recognized problem in the healthcare field. Other solutions to try and prevent this issue include placing the patient into an elevated position for the insertion of a central venous catheter, or to use a siphon that protects against the ingress of air in the infusion set, both of which have their drawbacks and limitations.

Accordingly, an apparatus and methods to remove the air bubbles from the IV line that does not have the disadvantages of the current methods and apparatus is needed. Current solutions are limited in various ways, including but not limited to, the capacity to hold air and fluid (where the current standard protocols are to remove the IV set after 72-96 hours), allowing more air bubbles to form, are limited in being non-refillable, and can sometimes move or relocate causing air to be introduced into the line. Thus, there exists a need to solve these current problems. There exists a need for a larger capacity to hold more air as it is removed from the fluid and to hold more fluid. This would allow for less required maintenance, reducing costs and time. There also exists a need to reduce costs in the development, manufacturing, maintenance, and upkeep of an air removal device by using fewer parts, no electricity in the device, no complicated and complex integrated parts that can break, and no obstructions in the chamber where the fluid flows into. There also exists a need to have a refillable apparatus, so that captured air can be removed and replaced with fluid by extracting the air through a valve in the device. There also exists a need for proper orientation of the device and the tube to avoid issues in function and performance. The inventions of the present disclosure provide these and other related advantages.

SUMMARY

In one embodiment, the present disclosure provides an air removal device for a fluid system. The air removal device includes a housing with an inlet for fluid communication with a fluid source, a fluid outlet for fluid communication with the blood stream, and an air outlet for air removal. In one aspect of at least one embodiment, the top of the air removal device provides for a tubing clip to secure the tube to ensure vertical orientation. The shell or body of the device can be made of any material that is safe, including but not limited to, plastics, polymers, synthetic compounds and other material known in the art. In one aspect of this embodiment, a chamber to store the liquid inside the shell or body is provided. This chamber can also provide storage for the air that is removed from the blood. The air rises to the top of the chamber towards the valve and does not travel through the tube to the patient.

In another embodiment of the present disclosure, an air removal device having a compact assembly designed to remove air from intravenous fluid tubing systems is provided. When air is introduced or occurs in a tubing system, it can lead to patient risk (embolism) or, at the very least, require the attention of the nursing staff. This embodiment of the present disclosure mitigates these concerns by allowing air to become separated from the fluid before being introduced into a patient. This embodiment is connected in-line with any IV tubing set as the last component before the pump (or patient, if the system is gravity fed). A clip feature at the top of the device attaches to the IV tubing to ensure the recommended orientation. Any air in the system is separated from the fluid as it enters the chamber. When air enters the chamber, it rises through the fluid to the top of the chamber and displaces a small amount of fluid. If necessary, after a large amount of air has been captured, the device can be refilled with fluid by attaching a syringe or other object or device to the valve and drawing out the air, which simultaneously refills the chamber with fluid. This allows the device to be easily refilled without removal from the pump for re-priming.

In yet another embodiment, the present disclosure provides for an apparatus comprising an outer wall, wherein the outer wall encompasses an interior chamber; an interior chamber, wherein the interior chamber holds a predetermined volume of fluid and air or gas, wherein the air inside the fluid rises to one end of the interior chamber, and wherein the fluid flows to the other end of the interior chamber; an inlet port, wherein the inlet port allows for fluid to ingress into the interior chamber, and wherein the inlet port is at a predetermined angle to the outer wall; an outlet port, wherein the outlet port allows for fluid to egress out of the interior chamber; and a tubing clip that is attached to the outer wall.

The present disclosure has many benefits over the current standard practices in the industry. First, the present disclosure allows for a larger capacity to hold more air as it is removed from the fluid and to hold more fluid. This would allow for less required maintenance, reducing costs and time. The present disclosure also allows for a reduction in costs in the development, manufacturing, maintenance, and upkeep of an air removal device by using less parts, no electricity in the device, no complicated and complex integrated parts that can break, and no obstructions in the chamber where the fluid flows into, where more viscous fluids can impede the evacuation of air or the obstructions can wear down or fail over time. The present disclosure also allows for an apparatus to have a refillable apparatus, so that captured air can be removed and replaced with fluid by extracting the air through a valve in the device. The present disclosure also allows a clip at the top of the device to ensure proper orientation of the device and the tube. The present disclosure also allows for a lower diameter than the current methods and systems for priming of similar apparatuses. For instance, priming for the apparatus in the present disclosure could be done at a minimum diameter of 0.35" but diameters significantly less than 0.35" prevented the apparatus from priming properly or easily. The present disclosure also allows for diameter, length, and volume variations depending on context and application and depending on capturing requirements. The present disclosure also allows for easy manufacturing using multiple processes and materials, such as using molded plastic or machined material using only basic operations, and provides an apparatus and method that does not require the use of components that can fail due to wear or the air or gas being a larger or entering into the chamber in a more turbulent manner than expected.

DRAWINGS

FIG. 6 depicts another embodiment of the present disclosure at 50% length.

FIG. 7 depicts yet another embodiment of the present disclosure at 150% length.

DETAILED DESCRIPTION

Figure 1:
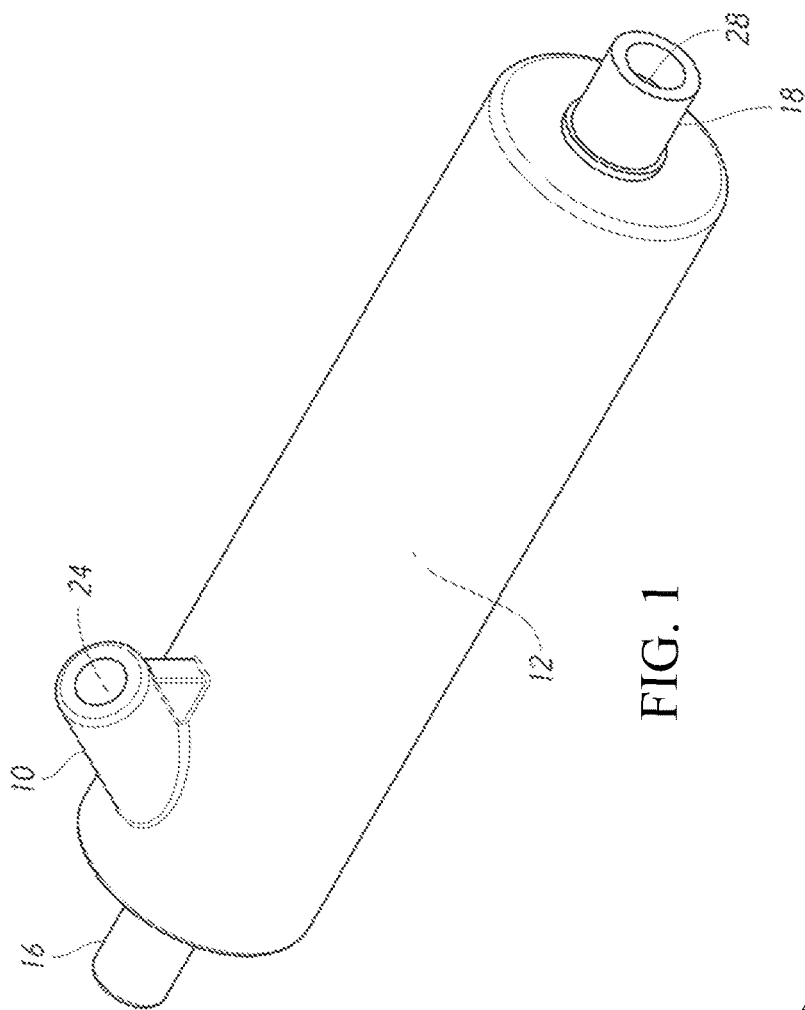
FIG. 1 depicts an embodiment from an angle with the inlet port on top according to the viewer and the valve closest to the viewer.
Figure 2:
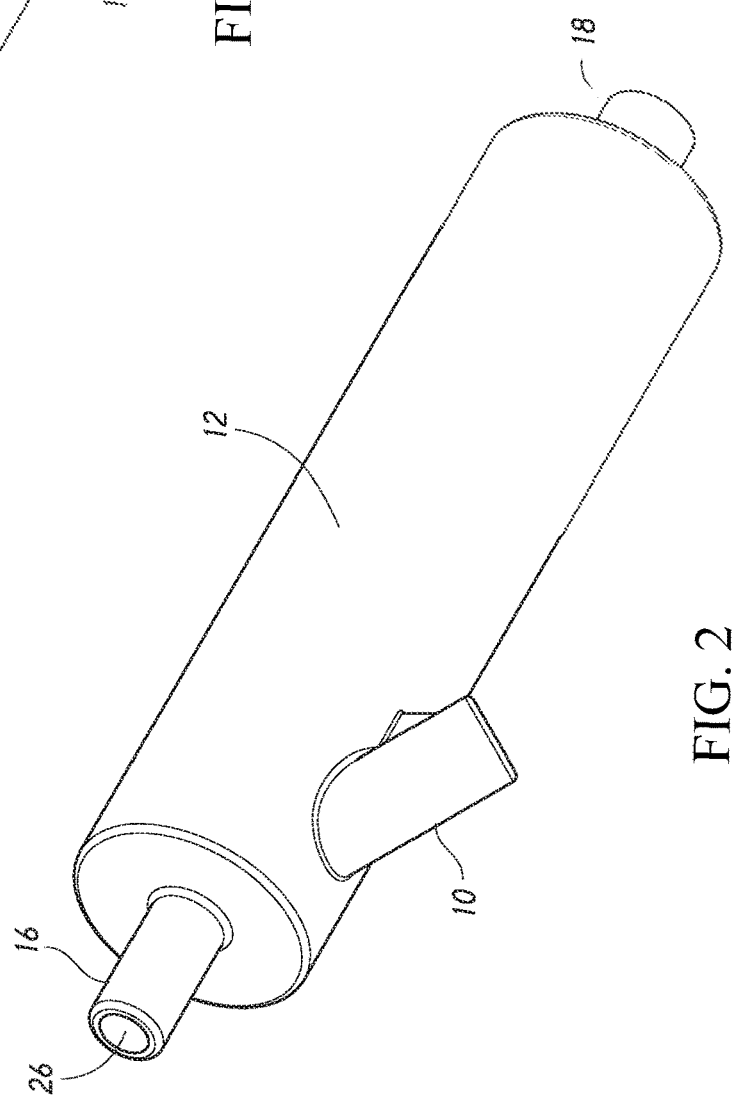
FIG. 2 depicts an embodiment from an angle with the inlet port on bottom according to the viewer and the outlet port closest to the viewer.
Figure 3:
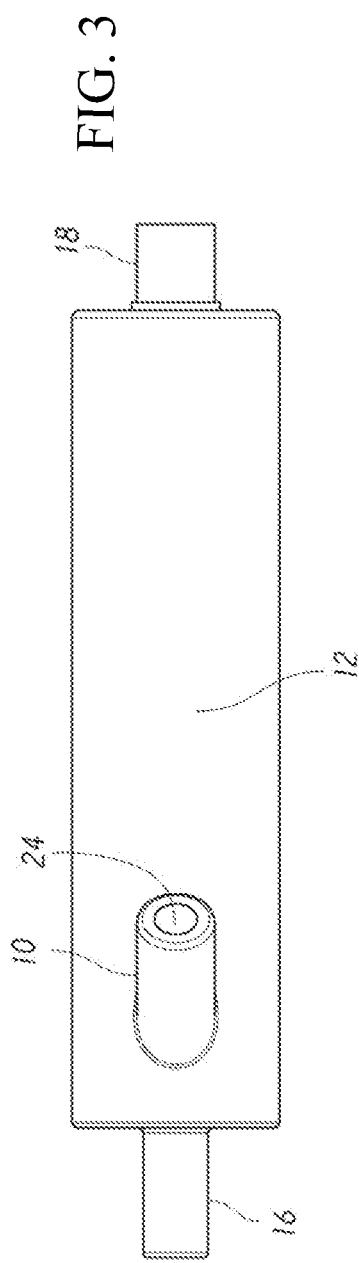
FIG. 3 depicts an embodiment from a top view with the inlet port closest to the viewer.
Figure 4:
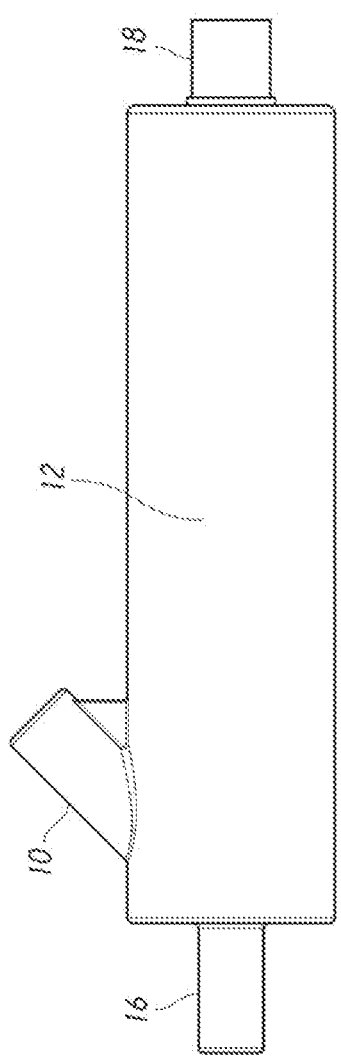
FIG. 4 depicts an embodiment from a side angle with the inlet port on top according to the viewer.
Figure 5:
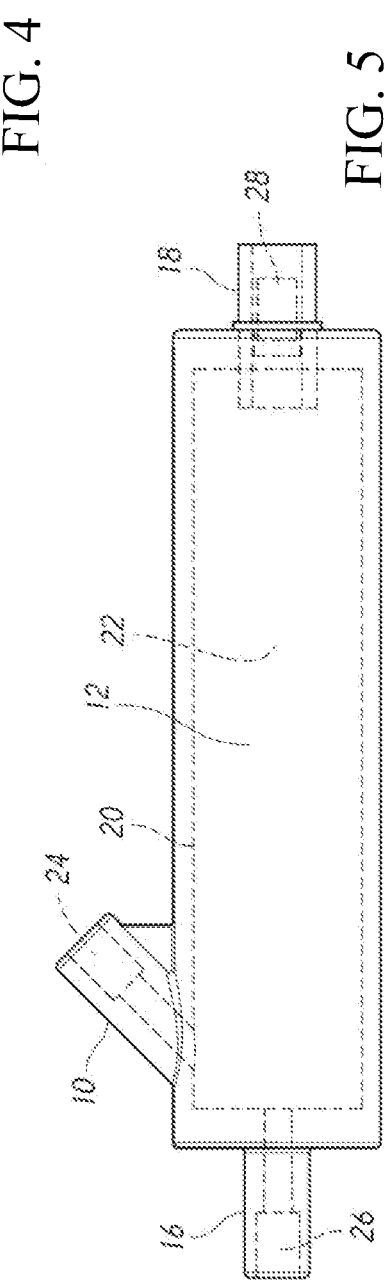
FIG. 5 depicts an embodiment from a side angle with the interior chamber visible, the inner wall, the interior of the inlet and outlet ports, and the interior of the valve being visible and with the inlet port on top according to the viewer.
Figure 8:
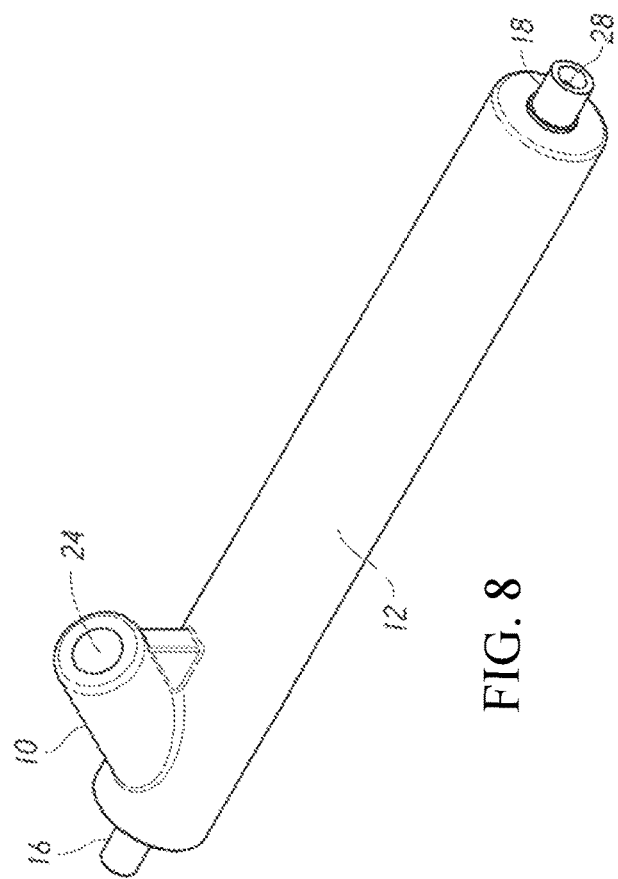
FIG. 8 depicts yet another embodiment of the present disclosure at 50% diameter.
Figure 9:
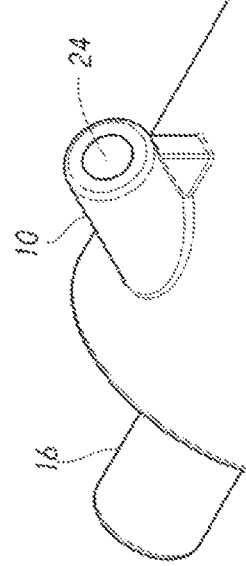
FIG. 9 depicts yet another embodiment of the present disclosure at 150% diameter.

A fluid delivery system is to include an air removal device (e.g., air catch, degasser, etc.). The fluid delivery system is configured to transport a fluid from a fluid source to a patient through generally closed passage, such as a passage provided by a length of tubing. In other embodiments, the fluid may be supplied from another source, such as a bottle or other closed, sterile container. The fluid delivery system may be used to deliver a variety of fluids, each containing varying levels of viscousness, to the blood vessel of a patient including, but not limited to, volume expanders (e.g., a saline solution (NaCl) as fluid replacement to fight dehydration, a glucose solution etc.), whole blood (e.g., a blood transfusion), blood components (e.g., red blood cells, plasma, platelets, etc.), or medicine (e.g., chemotherapy medicine, antibiotics, etc.)

The fluid delivery system may be coupled via an appropriate outlet connector to a catheter inserted through the skin and into a vein. The vein may be a peripheral vein (e.g., a vein in an arm or leg) or a central vein (e.g., a vein in the head or chest). In other embodiments, the fluid delivery system may deliver fluids into the body of the patient through another device, such as a port implanted in the skin of the patient. The outlet connector may be, for example, a male Luer connector that is permanently coupled to the outlet of the fluid delivery system (e.g., fused via heat or adhesive) and configured to be coupled to a corresponding female Luer connector. In other embodiments, the outlet of the fluid delivery system may be coupled to the catheter or another device with another type of connector (e.g., via a screw-type or pressure fitting, etc.).

In one embodiment, the flow rate of the fluid through the fluid delivery system and into the blood vessel of the patient is monitored and controlled by an infusion pump, a device that pumps directed levels of fluid to the patient. The infusion pump may deliver the fluid at a constant rate, or intermittently, either at a frequency determined by a caregiver or directly by the patient. A portion of the fluid delivery system passes through the infusion pump and directly interfaces with the infusion pump to control the flow rate of the fluid. In one embodiment, the fluid delivery system includes a cassette that is configured to fit into a corresponding socket of the infusion pump. In other embodiments, the fluid delivery system may lack a cassette and the infusion pump may be configured to receive a length of the tubing.

In other embodiments, an infusion pump may not be used, and the fluid delivery system may be a gravity drip system in which the IV bag is suspended above the patient and the fluid is delivered via gravity. In other embodiments, two or more fluid delivery systems may deliver fluids to a patient through a single catheter or other entry point. In such embodiments, one or more of the fluid delivery systems may use an infusion pump to control the flow rate while one or more other fluid delivery systems may be gravity feed systems.

The air removal device removes air bubbles from the fluid delivery system before the air bubbles reach the patient. By reducing the amount of air introduced into the blood vessel of the patient, the likelihood of complications related to air in the blood vessels, such as an air embolus causing harm to a patient, is dramatically reduced or eliminated.

Some infusion pumps may include a system to detect the presence of predetermined amount of air in the portion of the fluid delivery system passing through the infusion pump. Such an air-in-line detection system may be configured to take precautionary measures, such as halting the flow of fluid through the fluid delivery system, and/or alerting the caregiver. The alert may be, for example, an audio tone that is activated when air is detected and continues until the air is removed from the fluid delivery system and the infusion pump is reset. If positioned in the fluid delivery system upstream from an infusion pump, the air removal device reduces the occurrences of these alerts, which reduces the disturbances of both the patient and the caregiver. These repeated alerts are so common and disruptive to the medical process that the medical industry has coined the term, "alarm fatigue", to describe the phenomenon that medical professionals respond less often to the repeated alerts because they occur so frequently over time that they start to become less of a priority or ignored all together. Members of the medical community have identified "alarm fatigue" as one of the most important, if not the most important device related health hazard to patients. The inventions of the present disclosure provide a solution to alarm fatigue and other associated problems.

Fluid enters the fluid delivery system through an inlet, shown as an opening in a spike configured to pierce the IV bag. The spike is coupled to a drip chamber suspended below the IV bag. The fluid drips or otherwise flows out of the IV bag, through the opening, and into the drip chamber at a controlled rate. The size of the opening may be chosen to achieve a desired drop size and rate. When the fluid delivery system is primed (i.e., generally filled with fluid) and in use, the drip chamber is generally only partially filled with fluid. The fluid passes from the drip chamber to the remainder of the fluid delivery system while much of the air remains in the drip chamber or flows back into the IV bag through the opening.

From the drip chamber, the fluid may pass via the tubing through other components, such as a check valve and a connector, shown as forked tube or y-site. One fluid delivery system (e.g., a secondary set, piggyback set, etc.) may join or "piggyback" another fluid delivery system (e.g., a primary set) via the y-site. The y-site is a junction that includes a port (e.g., med port, injection port, etc.) which allows another substance to be introduced into the fluid delivery system. The substance may be, for example, a second fluid from a second fluid source. The second fluid may be delivered from a fluid source similar to the IV bag via tubing that interfaces with the y-site, from a syringe with a needle that pierces the port, or from a syringe that interfaces with the y-site in another way, such as with a connector (e.g., a Luer connector or another needleless connector). The two fluid delivery systems may each run continuously, one fluid delivery system may run continuously while the other fluid delivery system periodically adds the second fluid to the first fluid, or the first fluid delivery system may halt when the second fluid delivery system is active. The introduction of a second fluid into the fluid delivery system may introduce additional air into the system.

The gas removal apparatus is positioned along the fluid path between the inlet and the outlet of the fluid delivery system (e.g., joined to tubing through which the fluid flows from the opening to the outlet connector). The air removal device includes a housing defining an inlet, a fluid outlet, an air outlet, and a flow path along which fluid passes through the housing from the inlet to the fluid outlet. According to an exemplary embodiment, the housing is formed of a rigid, FDA-approved material. In one embodiment, the housing is generally formed as a main cylindrical portion and an angled cylindrical portion that intersects with the main cylindrical portion. The fluid outlet and the air outlet are provided on opposite ends of the main cylindrical portion and the inlet is provided at the distal end of the angled cylindrical portion. The arrangement of the outlets and on opposite ends of the housing facilitates the removal of air from the fluid flow path.

The cylindrical portions have inner diameters that are configured to receive the tubing, such as a standard ¼" diameter polymer (e.g., polypropylene, nylon, etc.) tubing. In other embodiments, the cylindrical portions may be sized to receive tubing of another diameter. Tubing is coupled to the inlet and the outlet with an appropriate water-tight coupling mechanism to form a sterile, closed passage from the tubing coupled to the inlet, through the interior of the housing along the flow path, to the tubing coupled to the fluid outlet. The tubing may be permanently coupled to the housing (e.g., by adhesive, by heat staking, etc.) or may be temporarily coupled to the housing, such as with a Luer connector or another appropriate screw-type or pressure fitting.

In yet another embodiment, the housing may be otherwise shaped. For example, the interior of the housing may be generally flattened, or may have a rectangular cross-section. In other embodiments, the inlet and outlets and may be otherwise arranged relative to each other. For example, the housing may be a T-shaped body. In yet another embodiment, the shape of the body can be any configuration that allows the air to rise to the top and be separated from the fluid while the fluid egresses from the fluid delivery system.

The air chamber is shown according to an exemplary embodiment. The air chamber provides a cavity configured to have an internal volume that is sufficient to contain any air that would be typically contained in an IV bag as well as air that may be introduced into the fluid delivery system from other sources (e.g., a secondary line or a syringe via a y-site or other connector. The result allows the device to safely contain air from the fluids until it can be separated or removed.

In yet another embodiment, the air chamber is a flexible, tubular body with a sealed end. The air chamber is formed from an FDA-approved material that does not react in the presence of the fluid. The air chamber may be formed, for example, from a suitable polymer (e.g., polypropylene, nylon, etc.). The air chamber is coupled to the air outlet of the housing with an appropriate air-tight coupling mechanism to form a sterile, closed passage from the interior of the housing to the interior of the air chamber.

In yet other embodiments, the air chamber may include a flexible bladder as a caregiver may not actively alter the volume of the air chamber after priming the fluid supply system. In the compressed configuration, the bladder is not inflated. As air is removed from the fluid and enters the air chamber, the bladder becomes inflated with the air removed from the fluid. The air chamber may further include a rigid outer housing to protect the bladder from damage or accidental compression. The outer housing includes openings allowing the inflating bladder to displace air out of the interior of the housing.

In yet another embodiment, the air may not be collected in the air chamber. Instead, air may exit the fluid delivery system through an air outlet and subsequently pass through a device, such as a low pressure check valve, to the atmosphere. The check valve allows air to exit the fluid supply system without allowing outside contaminants to enter the fluid supply system.

In yet another embodiment, the air may not be collected in the air chamber but may be routed to another sealed body. For example, the air removal device may include a return line coupled between the air outlet and another chamber, such as the drip chamber or the IV bag (e.g., through a port in the upper portion of the IV bag, above the level of the fluid contained therein).

Air may be effectively removed from the fluid with the air removal device even if the air does not enter the air chamber. For example, air bubbles trapped by the insert in the intermediate chambers formed by the gaps are prevented from continuing with the fluid to be expelled out of the outlet connector and into the patient's blood vessel. Similarly, air may displace fluid not only from the interior of the air chamber as described above, but also from the upper portion of the housing (e.g., the portion of the main cylindrical portion proximate the air outlet) outside of the flow path 38 without interrupting the flow of fluid through the fluid delivery system.

Another embodiment of the disclosed invention of the fluid delivery system is configured similarly to the fluid system described above. The fluid delivery system includes an additional air removal device in series with the air removal device. Both air removal devices are provided upstream from the cassette, pump, or similar device. The second air removal device is positioned downstream from the first air removal device such that an inlet of the second air removal device is coupled to the fluid outlet of the first air removal device. The second air removal device is therefore positioned to capture any air that is able to pass the first air removal device and divert it away from the fluid continuing to the cassette, thereby reducing the likelihood that air will reach the cassette, pump, or similar device and trigger an alarm by the pump. A multitude of air removal devices may be combined to further reduce the likelihood that air will reach the cassette and in turn the patient. In another embodiment, pumps could accommodate the air removal device just prior to the sensor that is detecting air in the line, eliminating the problem of air developing inside the pump, shutting down the pump, and sounding the alarm. In yet another embodiment, air bubbles rise from below the pump and then get into the pump and contribute to causing the alarm to go off and shut the pump down. In this embodiment, the present invention could be placed just below the pump such that these rising air bubbles would get captured on their way up before they could get into the pump.

In yet another embodiment, the fluid delivery system is configured similar to the fluid system described above. The fluid delivery system includes one or more additional air removal devices in parallel or series with the air removal device. The air removal device is provided downstream from the cassette. Some very small bubbles may be able to pass the first air removal device.

In yet another embodiment, the apparatus of the present disclosure is integrated into another medical device (e.g., an infusion pump), provided downstream and/or upstream from the medical device and multiple apparatus are used in combination with the medical device to ensure that little to no air ever passes through the medical device and into the patient.

Small bubbles may also be able to pass through the pump without triggering the alarm. While such small bubbles may be sufficiently decreased in size such that they have a negligible effect on an adult, they may still have an adverse effect on a small child, such as a small child in a neonatal intensive care unit. According to an exemplary embodiment, the second air removal device may be configured to capture small bubbles that are able to pass the first air removal device. The second air removal device is therefore positioned and configured to capture any air that is able to pass the first air removal device and divert it away from fluid flow to the outlet connector, thereby reducing the likelihood that air will reach the patient.

In yet another embodiment, the present disclosure provides for an apparatus comprising an outer wall 12, wherein the outer wall 12 encompasses an interior chamber 22; an interior chamber 22, wherein the interior chamber 22 holds a predetermined volume of fluid and air or gas, wherein the air inside the fluid rises to one end of the interior chamber 22, and wherein the fluid flows to the other end of the interior chamber 22; an inlet port 24, wherein the inlet port 24 allows for fluid to ingress into the interior chamber 22, and wherein the inlet port 24 is at a predetermined angle to the outer wall 12; an outlet port 26, wherein the outlet port 26 allows for fluid to egress out of the interior chamber 22; and a tubing clip 14 that is attached to the outer wall 12.

In yet another embodiment, the present disclosure provides for an apparatus comprising of an outer wall 12 that encompasses an interior chamber 22, an interior chamber 22 to hold fluid and air and gas and is surrounded by an inner wall 20, an inlet port 24 to allow for fluid to ingress into the interior chamber 22, wherein the air or gas inside the fluid rises to one end of the chamber, an outlet port 26 to allow for fluid to egress out of the interior chamber 22, a valve 28 to allow for air or gas to egress, and a tubing clip 14 that is attached to the outer wall 12.

In yet another embodiment, the present disclosure provides for an apparatus comprising of an outer wall 12 that encompasses an interior chamber 22; an interior chamber 22 that holds a predetermined volume of fluid and air or gas and is surrounded by an inner wall 20, wherein the air inside the fluid rises to one end of the interior chamber 22, and wherein the fluid flows to the other end of the interior chamber 22; an inlet port 24 that allows for fluid to ingress into the interior chamber 22, and the inlet port 24 is at a predetermined angle to the outer wall 12; an outlet port 26 that allows for fluid to egress out of the interior chamber 22; a valve 28 that is closed to trap the air or gas until opened to allow for the air or gas to egress from the interior chamber 22; and a tubing clip 14 that is attached to the outer wall 12.

In yet another embodiment, the present disclosure provides for an apparatus comprising of an outer wall 12 that encompasses an interior chamber 22, wherein the outer wall 12 has two flat ends; an interior chamber 22 to hold about 3 ml of fluid and is surrounded by an inner wall 20; an inlet port 24 that is attached to the outer wall 12 at a predetermined angle from the outer wall 12; an outlet port 26 on one end of the outer wall 12, wherein the outlet port 26 and the inlet port 24 at a minimum of 0.35" distance from each other; a valve 28 on the opposite end of the outer wall 12 as the outlet port 26, wherein the valve 28 and the outlet port 26 are on opposite ends of the outer wall 12 and are aligned along a center axis; and a tubing clip 14 that is attached to the outer wall 12.

In yet another embodiment, the present disclosure provides for an apparatus comprising of an outer wall 12, wherein the outer wall 12 encompasses an interior chamber 22; an interior chamber 22 to hold a minimum of 3.3 ml of fluid; an inlet port 24, wherein the inlet port 24 is attached to the outer wall 12 at a degree that is less than perpendicular and greater than parallel to the outer wall 12; an outlet port 26 on one end of the outer wall 12, wherein the outlet port 26 and the inlet port 24 are at a minimum of 0.35" distance from each other; a valve 28 on the opposite end of the outer wall 12 as the outlet port 26, wherein the valve 28 and the outlet port 26 are on opposite ends of the outer wall 12 and are aligned along a center axis, and wherein the valve 28 is closed to tap air or gas inside the interior chamber 22; and a tubing clip 14 that is attached to the outer wall 12, wherein the tubing clip 14 can hold a tube of at least 2 mm in diameter.

In yet another embodiment, the outer wall 12 is 2" in length. In another embodiment, the outer wall 12 is 2.1" in length. In yet another embodiment, the outer wall 12 is 2.2" in length. In yet another embodiment, the outer wall 12 is 2.3" in length. In yet another embodiment, the outer wall 12 is 2.4" in length. In yet another embodiment, the outer wall 12 is 2.5" in length. In yet another embodiment, the outer wall 12 is 2.6" in length. In yet another embodiment, the outer wall 12 is 2.7" in length. In yet another embodiment, the outer wall 12 is 2.8" in length. In yet another embodiment, the outer wall 12 is 2.9" in length. In yet another embodiment, the outer wall 12 is 3.0" in length.

The fluid includes, but is not limited to, blood, water, saline, ringer's solution, chemotherapeutic agents, hydraulic fluid, brake fluid, motor oil, and any other fluid.

In yet another embodiment, the outer wall 12 comprises of a material that is safe to use in fluid transport or communication and is constructed using a material including, but not limited to, metal, plastic, glass. In one embodiment, the outer wall 12 is about 16 mm in diameter. In another embodiment, the outer wall 12 is at least 2 mm thick.

In yet embodiment, the interior chamber 22 can hold a predetermined volume of air or gas. In one embodiment, this predetermined volume is about 10% air or gas. In another embodiment, this predetermined volume of air is 15% air or gas. In yet another embodiment, this predetermined volume is 20% air or gas. In yet another embodiment, this predetermined volume is 25% air or gas. In yet another embodiment, this predetermined volume is 30% air or gas. In yet another embodiment, this predetermined volume is 35% air or gas. In yet another embodiment, this predetermined volume is 40% air or gas. In yet another embodiment, this predetermined volume is 45% air or gas. In yet another embodiment, this predetermined volume is 50% air or gas. However, this predetermined volume of air or gas is not intended to be limiting on the ranges of predetermined volumes within embodiments of the device and method as disclosed herein. Thus, the predetermined volume could be any percentage as long as the volume level of trapped air or gas remains above the inlet port 24.

In order to reduce costs and improve stability associated with the development, manufacturing, maintenance, and use of the present disclosure, and to provide a benefit over the standard practice in the industry, the present disclosure is to be made in a simple form without need for unnecessary components. The standard practice being the use of complicated devices with many parts and with many of these parts are moving, use electronics or power, or are small or integrated with other parts that make the device complicated to keep maintained. In one embodiment, the interior chamber 22 is empty and free of any diffuser or other obstacle to allow for the free flow of fluid and air or gas. In another embodiment, the present disclosure does not have any electronic control units or any electronics. This allows for the costs associated with the development, manufacturing, and maintenance to be reduced. The removal of air from the fluid is a passive feature of the present disclosure. There are no requirements for a sensor to detect air in the fluid. The air will rise to one end of the interior chamber 22 without the need for external force or necessary obstacles.

In yet another embodiment, the interior chamber 22 has a volume of about 1 ml. In another embodiment, the interior chamber 22 has a volume between about 1 to 2 ml. In yet another embodiment, the interior chamber 22 has a volume of about 2 ml. In yet another embodiment, the interior chamber 22 has a volume of about 3 ml. In yet another embodiment, the interior chamber 22 has a volume of about 4 ml. In yet another embodiment, the interior chamber 22 has a volume of about 5 ml. In yet another embodiment, the interior chamber 22 has a volume of about 6 ml. In yet another embodiment, the interior chamber 22 has a volume of about 7 ml. In yet another embodiment, the interior chamber 22 has a volume of about 8 ml. In yet another embodiment, the interior chamber 22 has a volume of about 9 ml. In yet another embodiment, the interior chamber 22 has a volume of about 10 ml. In yet another embodiment, the interior chamber 22 has a volume of about 11 ml. In yet another embodiment, the interior chamber 22 has a volume of about 12 ml. In yet another embodiment, the interior chamber 22 has a volume of about 13 ml. In yet another embodiment, the interior chamber 22 has a volume of about 14 ml. In yet another embodiment, the interior chamber 22 has a volume of about 15 ml.

In yet another embodiment, the interior chamber 22 has a diameter of about 0.30". In another embodiment, the interior chamber 22 has a diameter of about 0.31". In yet another embodiment, the interior chamber 22 has a diameter of about 0.32". In yet another embodiment, the interior chamber 22 has a diameter of about 0.33". In yet another embodiment, the interior chamber 22 has a diameter of about 0.34". In yet another embodiment, the interior chamber 22 has a diameter of about 0.35". In yet another embodiment, the interior chamber 22 has a diameter of about 0.36". In yet another embodiment, the interior chamber 22 has a diameter of about 0.37". In yet another embodiment, the interior chamber 22 has a diameter of about 0.38". In yet another embodiment, the interior chamber 22 has a diameter of about 0.39". In yet another embodiment, the interior chamber 22 has a diameter of about 0.40". In yet another embodiment, the interior chamber 22 has a diameter of about 0.3" to about 0.7". In one embodiment, the interior chamber 22 has a fixed diameter from one end to the other. In another embodiment, the interior chamber 22 has a greater diameter on one end than the other. For instance, each of the above diameters for the interior chamber 22 could apply to either end or both ends of the interior chamber 22. In yet another embodiment, the above diameters for the interior chamber 22 apply to the entire length of the interior chamber 22.

In yet another embodiment, the inner wall 20 comprises of a material that is safe to use in fluid transport or communication and is constructed using a material including, but not limited to, metal, plastic, glass. In one embodiment, the inner wall 20 is about 2 mm thick. In one embodiment, the inner wall 20 is coated with a substance, including, but not limited, to polytetrafluoroethylene or PTFE, or any other substance that is safe to use in fluid communication systems and devices, such as for medical purposes, and hydraulic systems and devices. In another embodiment, the inner wall 20 is not coated with a substance.

In yet another embodiment, the inlet port 24 comprises of a material that is safe to use in fluid transport or communication and is constructed using a material including, but not limited to, metal, plastic, glass. In yet another embodiment, the inlet port 24 is about 15 mm in length. In another embodiment, the inlet port 24 is about 16 mm in length. In yet another embodiment, the inlet port 24 is about 17 mm in length. In yet another embodiment, the inlet port 24 is about 18 mm in length. In yet another embodiment, the inlet port 24 is about 19 mm in length. In yet another embodiment, the inlet port 24 is about 20 mm in length.

In yet another embodiment, the inlet port 24 is about 10 degrees from the outer wall 12. In another embodiment, the inlet port 24 is 15 degrees from the outer wall 12. In yet another embodiment, the inlet port 24 is 20 degrees from the outer wall 12. In yet another embodiment, the inlet port 24 is 25 degrees from the outer wall 12. In yet another embodiment, the inlet port 24 is 30 degrees from the outer wall 12. In yet another embodiment, the inlet port 24 is 35 degrees from the outer wall 12. In yet another embodiment, the inlet port 24 is 40 degrees from the outer wall 12. In yet another embodiment, the inlet port 24 is 45 degrees from the outer wall 12. In yet another embodiment, the inlet port 24 is 90 degrees from the outer wall 12. In yet another embodiment, the inlet port 24 is at an angle that is less than perpendicular and greater than parallel to the outer wall 12. In yet another embodiment, the inlet port 24 is at an angle that is greater than perpendicular and lesser than parallel to the outer wall 12.

Figures 10, 11:
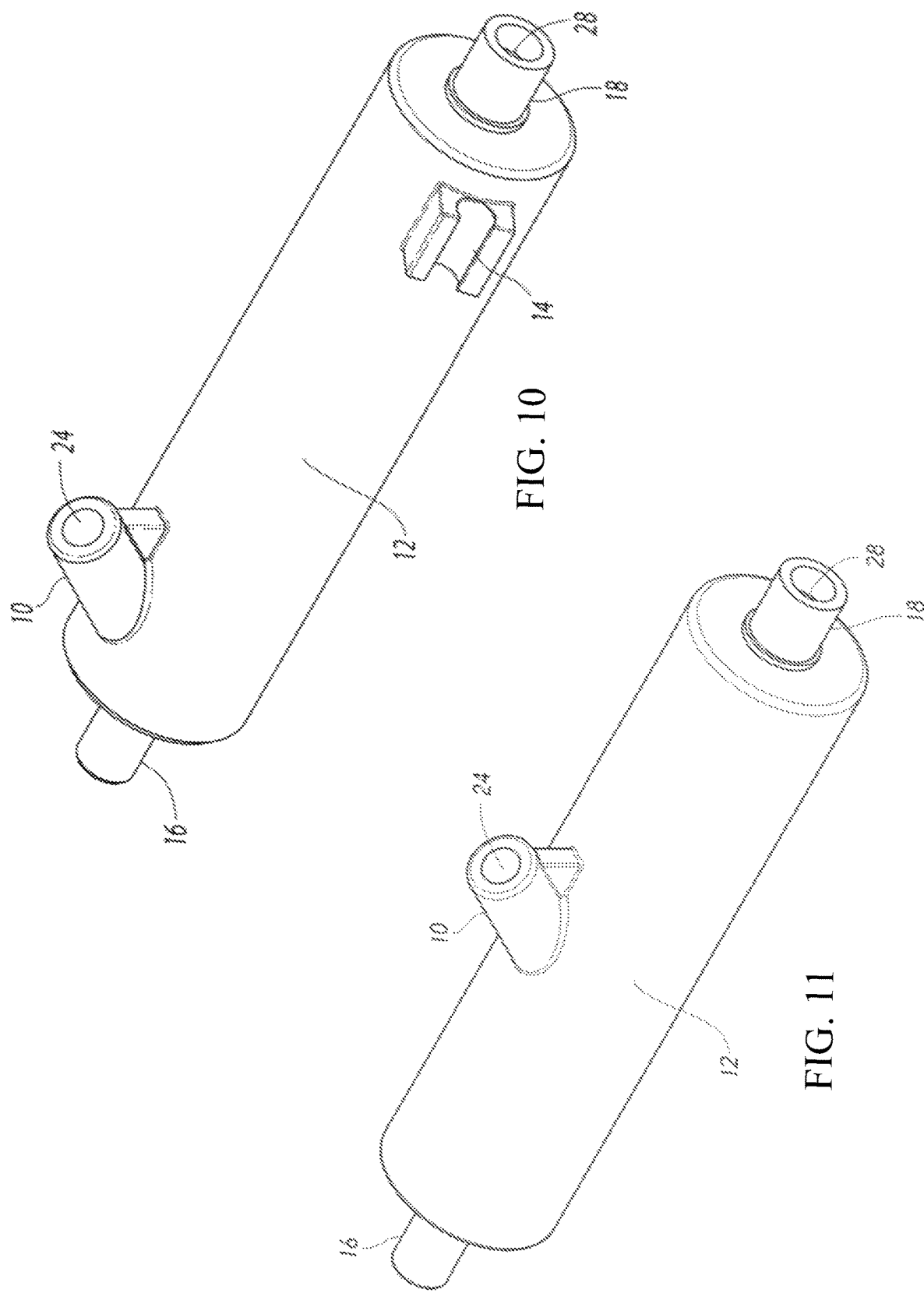
FIG. 10 depicts yet another embodiment of the present disclosure with the tubing clip.
FIG. 11 depicts yet another embodiment of the present disclosure with the inlet port in the middle of the apparatus and between the outlet port and the valve.
Figure 12:
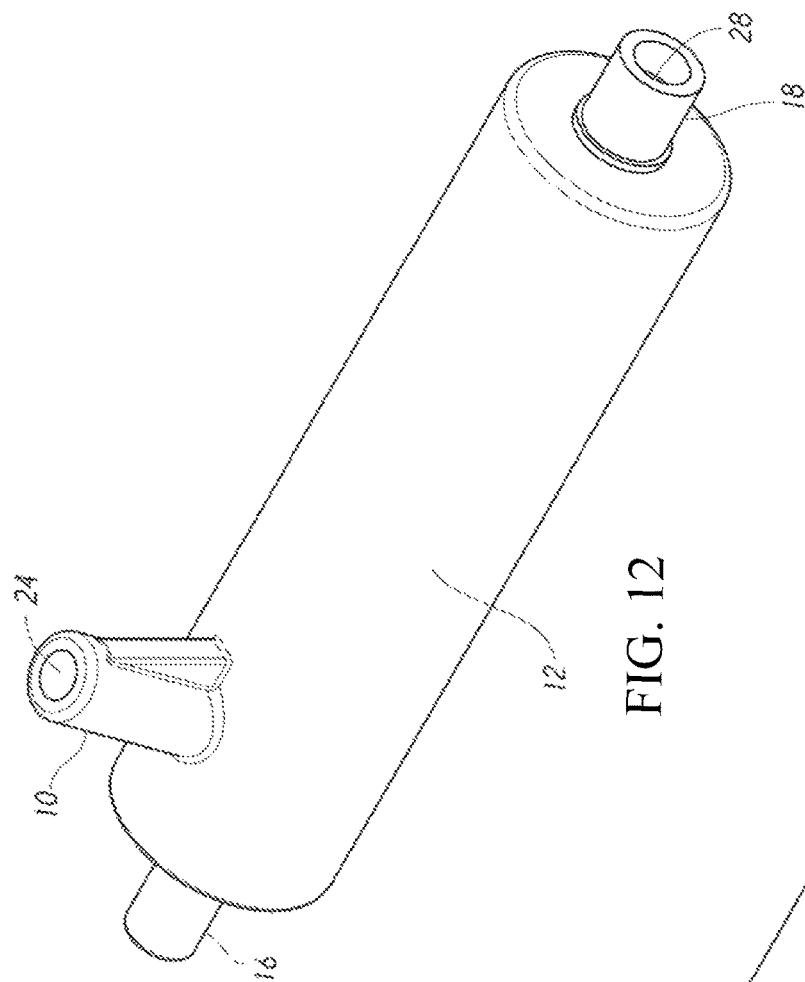
FIG. 12 depicts yet another embodiment of the present disclosure with the inlet port at 75 degrees from the outer wall.
Figure 13:
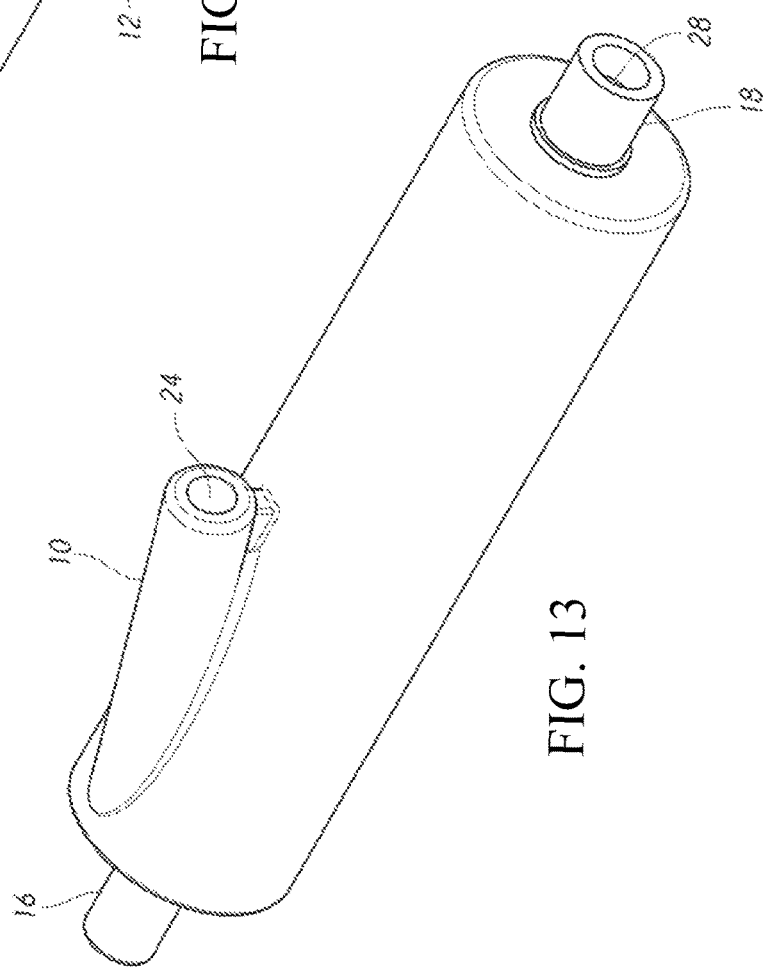
FIG. 13 depicts yet another embodiment of the present disclosure with the inlet port at 15 degrees from the outer wall.
Figure 14:
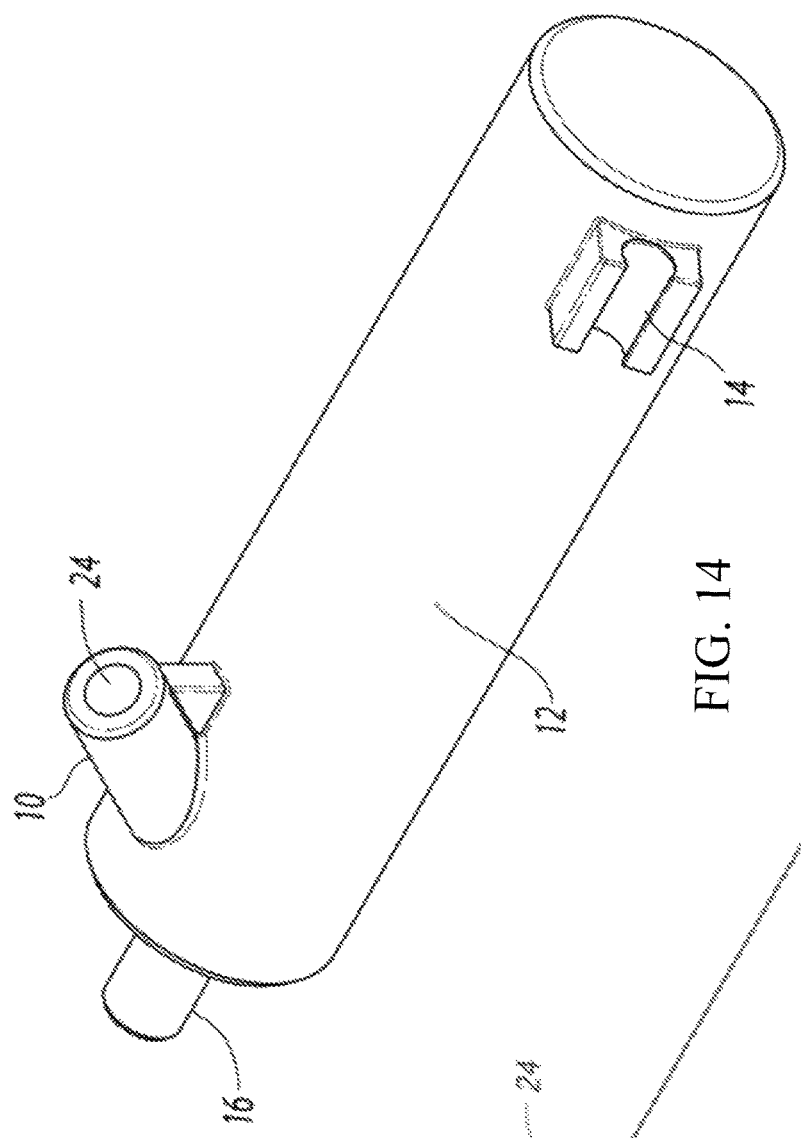
FIG. 14 depicts yet another embodiment of the present disclosure without the valve and with the tubing clip on top.
Figure 15:
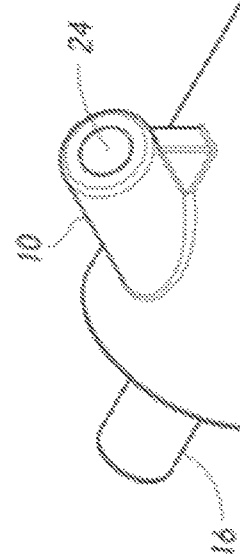
FIG. 15 depicts yet another embodiment of the present disclosure without the valve and without the tubing clip.
Figure 16:
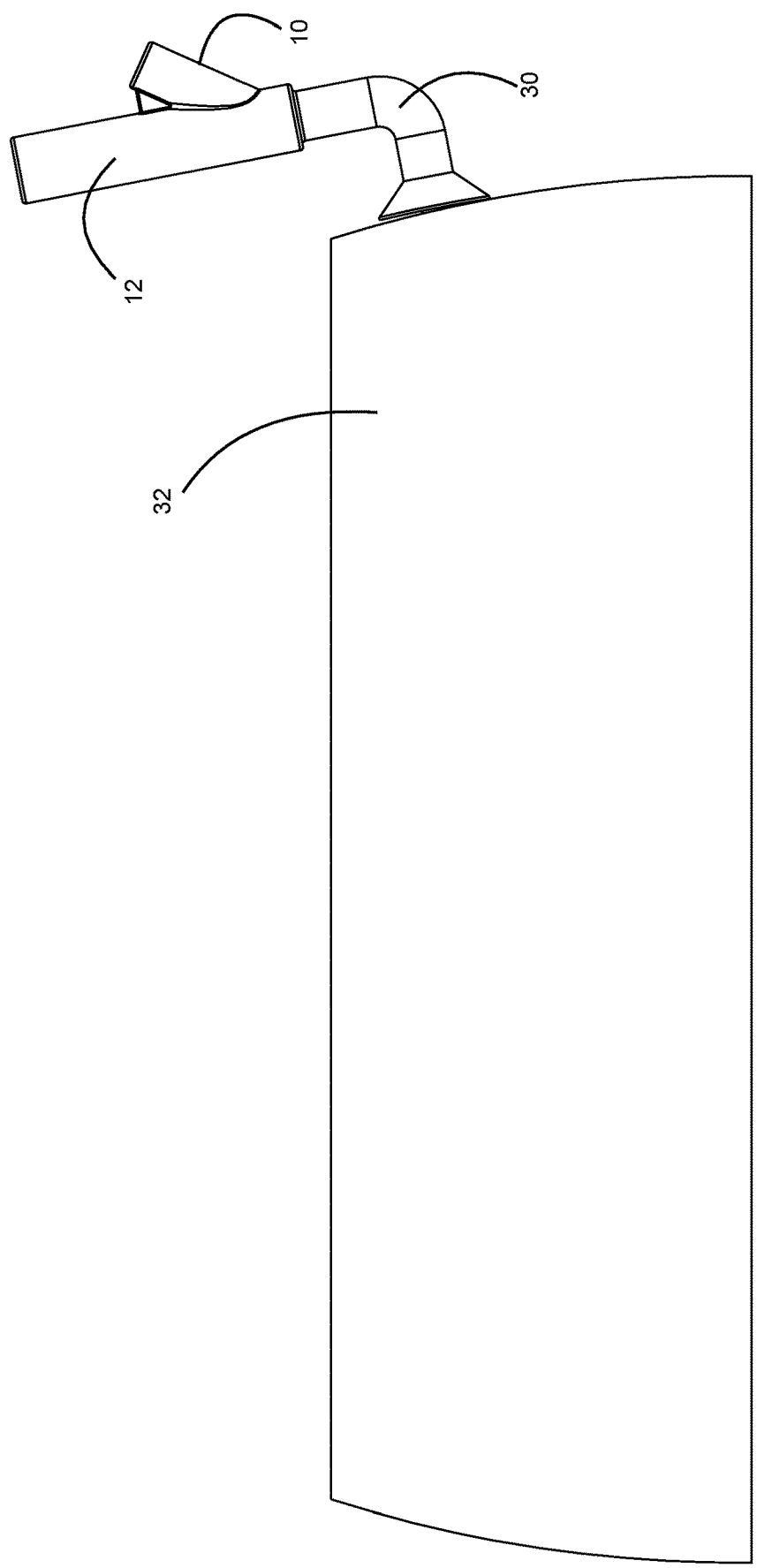
FIG. 16 depicts yet another embodiment of the present disclosure with a connector connected to the outlet port to a pump as seen from a side view.
Figure 17:
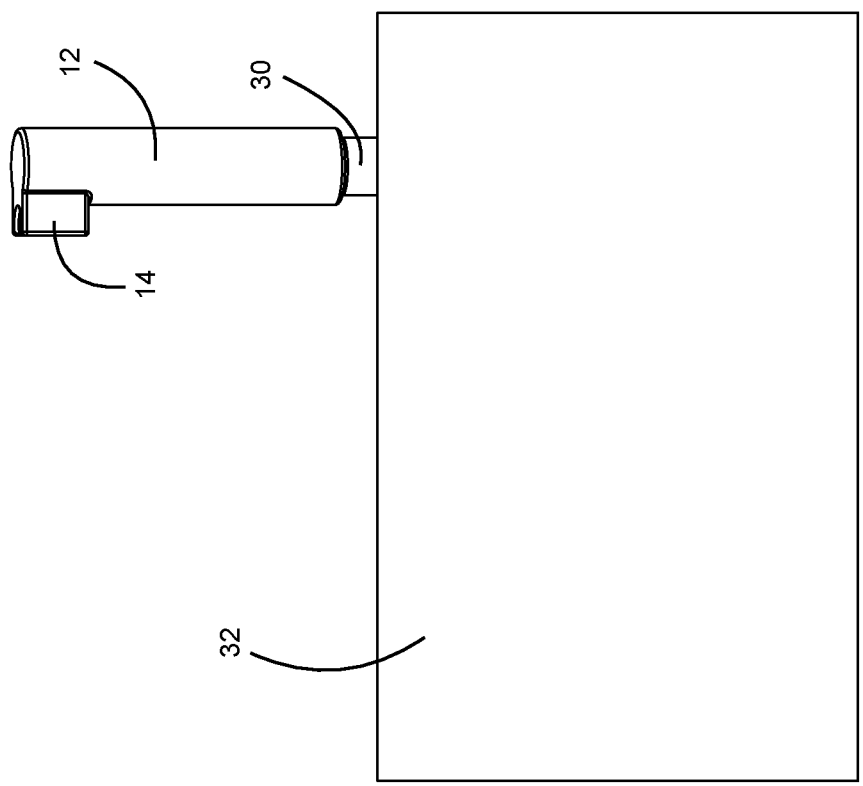
FIG. 17 depicts yet another embodiment of the present disclosure with a connector connected to the outlet port to a pump as seen from another side view.
Figure 18:
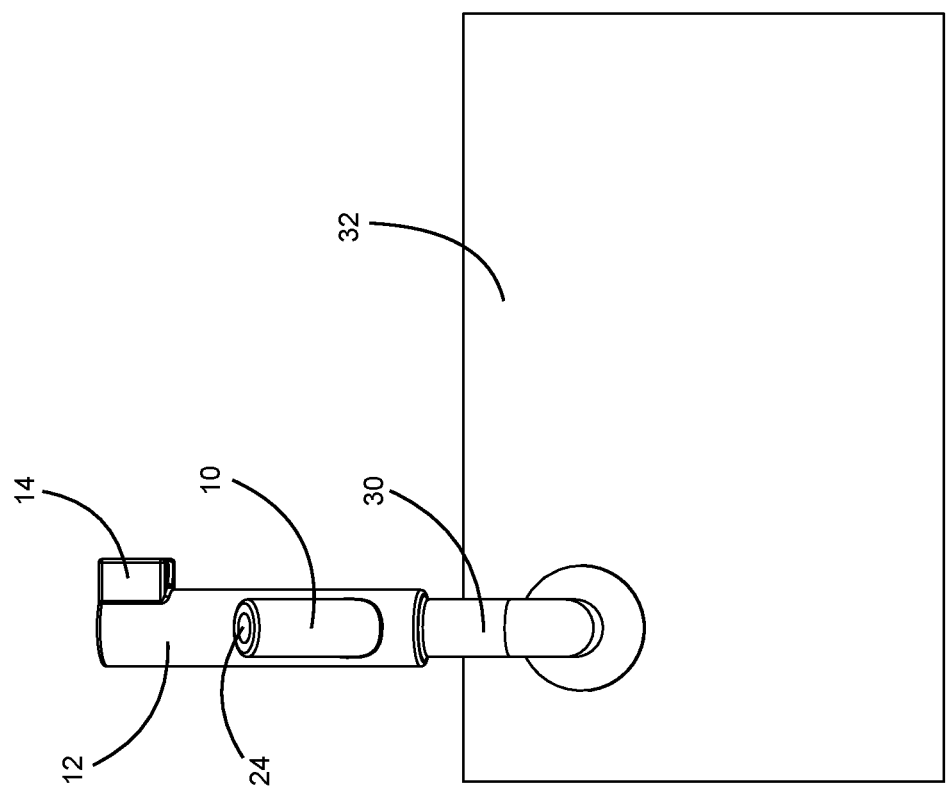
FIG. 18 depicts yet another embodiment of the present disclosure with a connector connected to the outlet port to a pump as seen from another side view.
Figure 19:
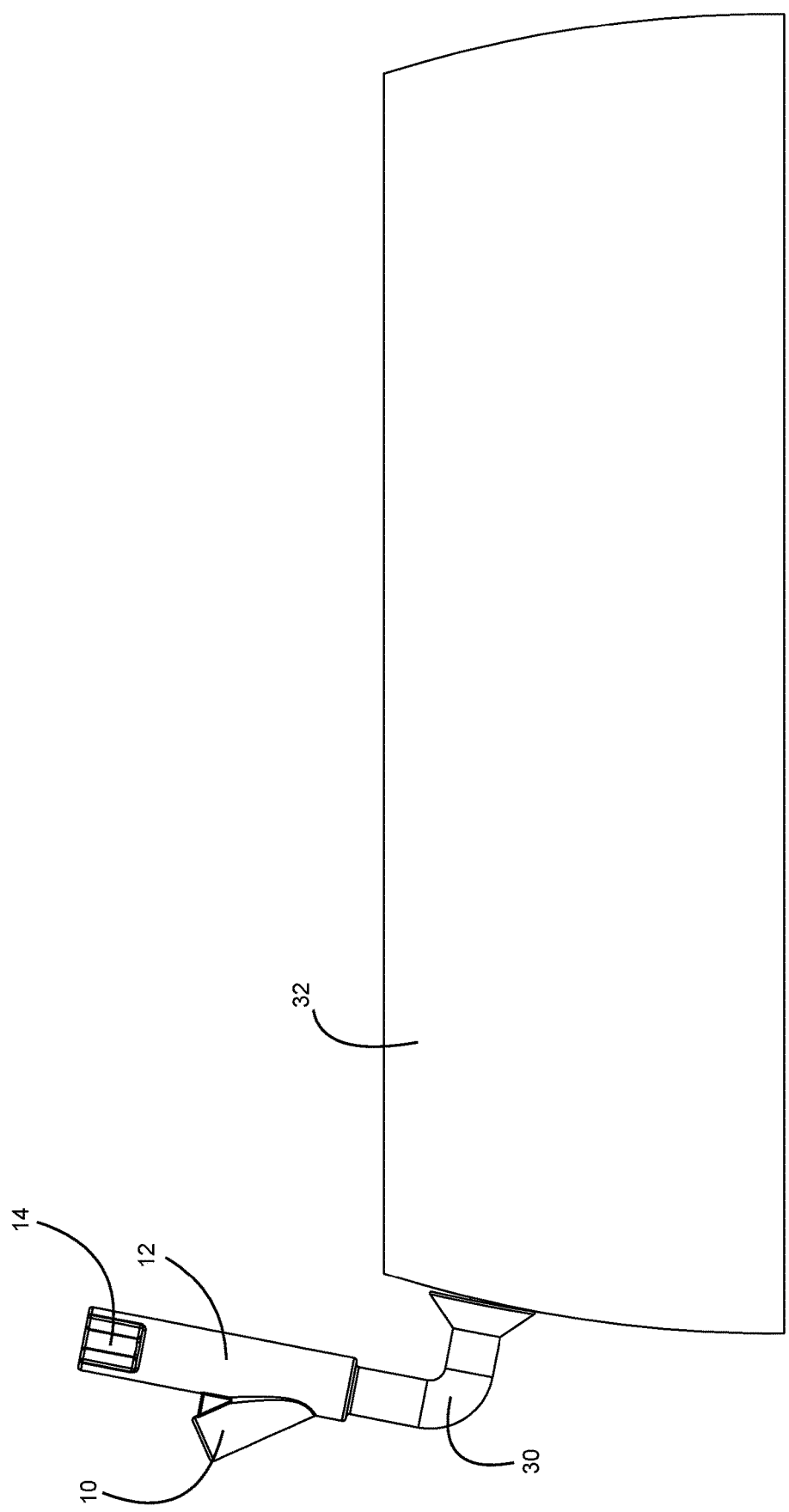
FIG. 19 depicts yet another embodiment of the present disclosure with a connector connected to the outlet port to a pump as seen from another side view.
Figure 20:
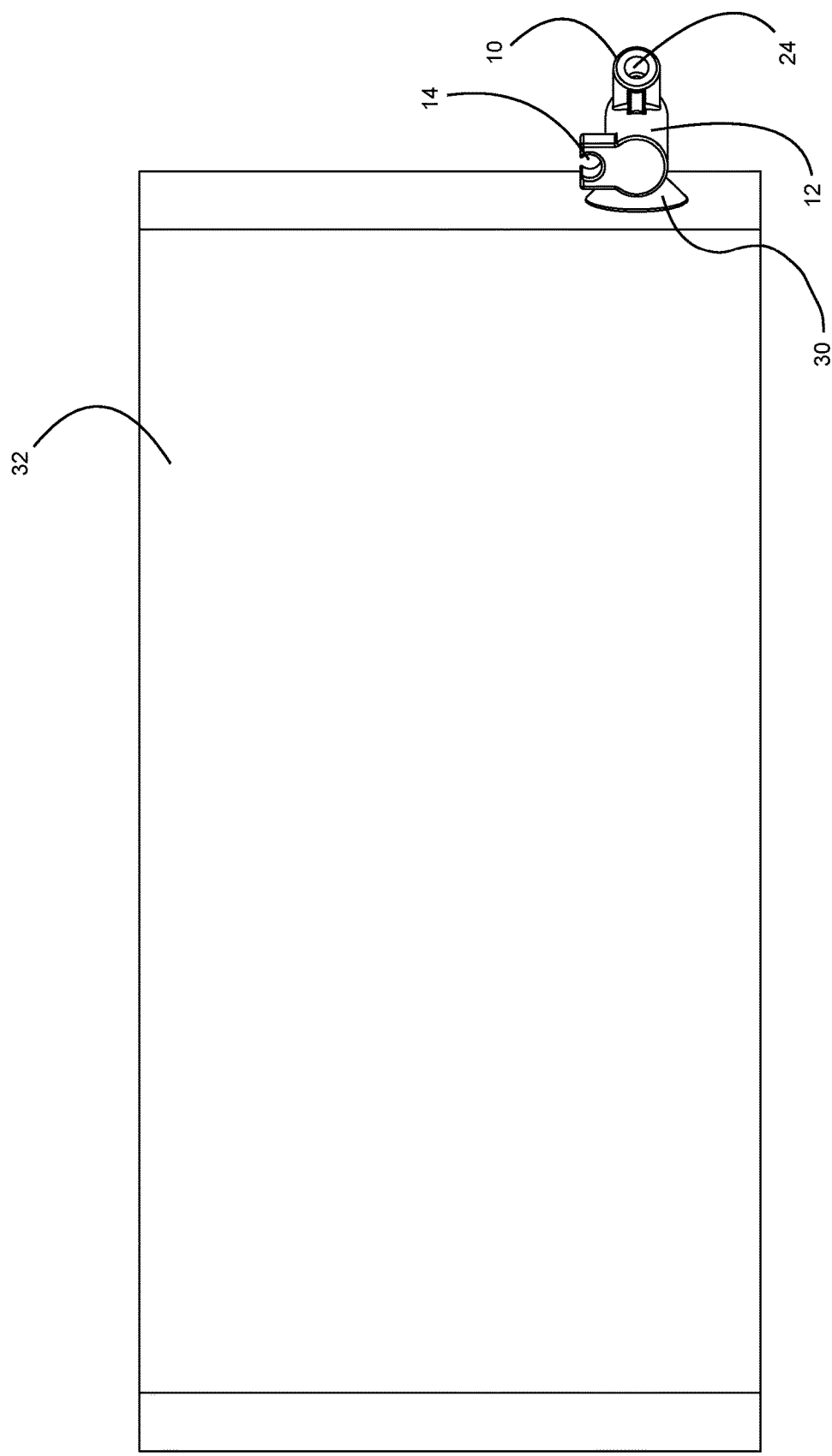
FIG. 20 depicts yet another embodiment of the present disclosure with a connector connected to the outlet port to a pump as seen from the top view.
Figure 21:
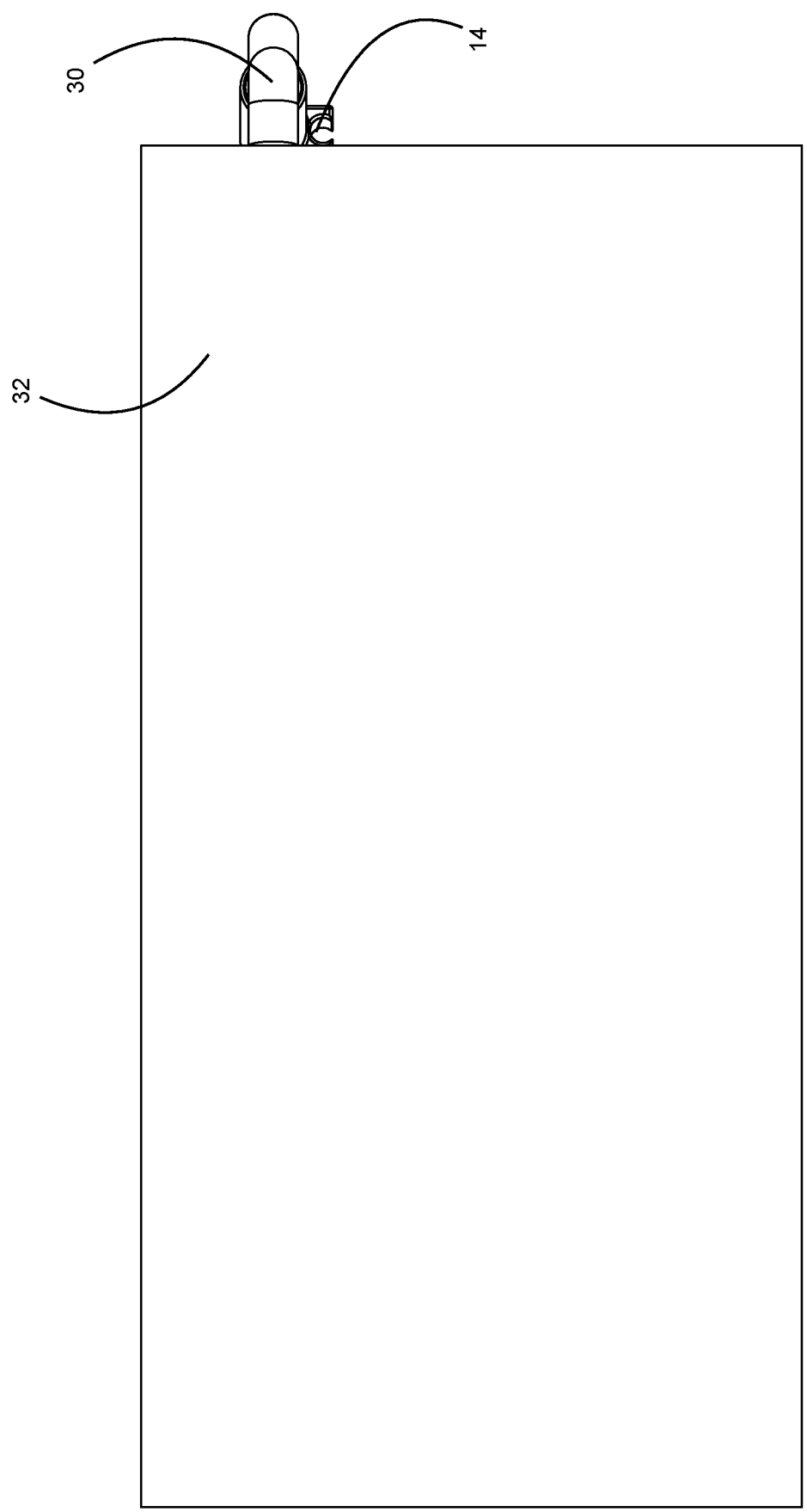
FIG. 21 depicts yet another embodiment of the present disclosure with a connector connected to the outlet port to a pump as seen from the bottom view.
Figure 22:
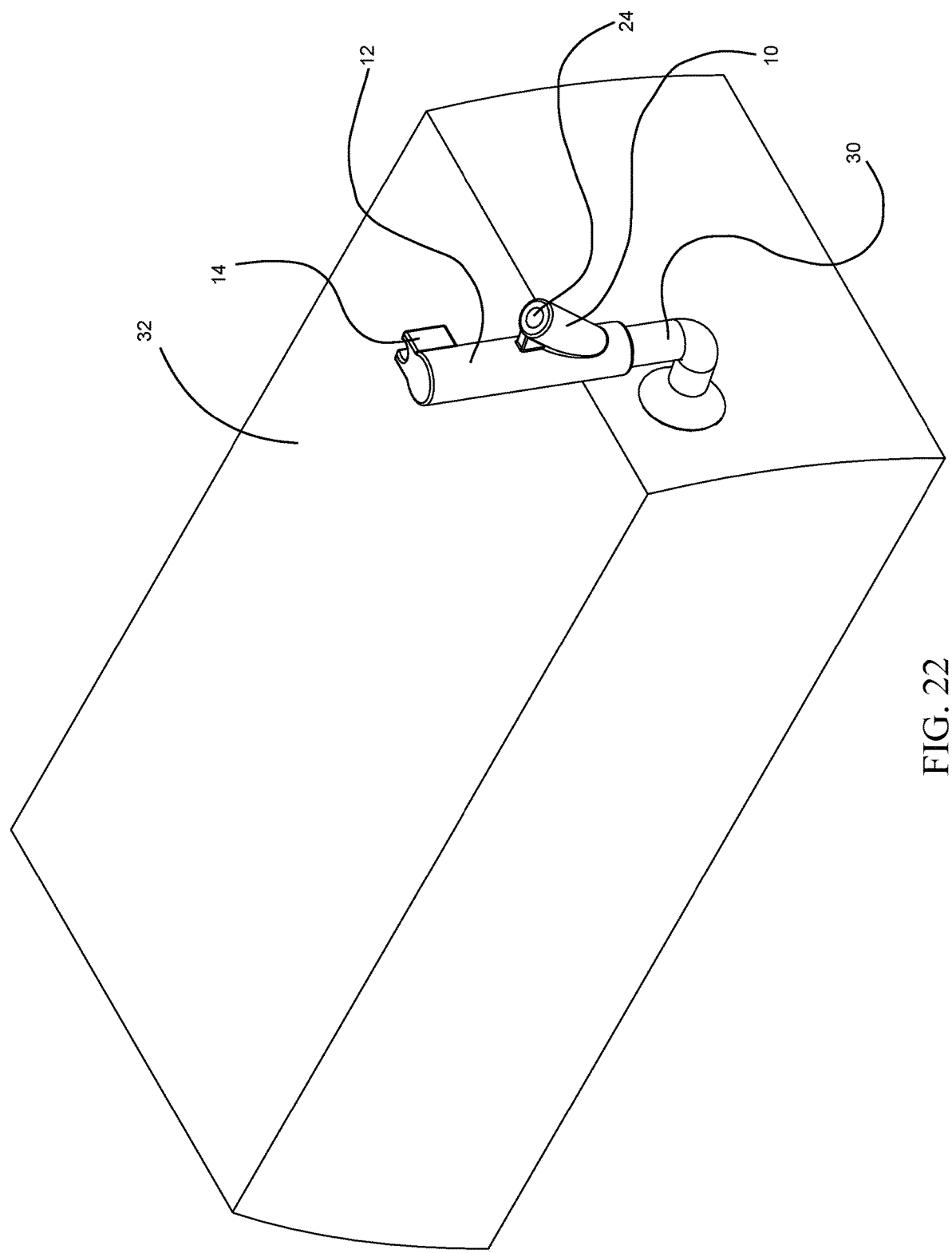
FIG. 22 depicts yet another embodiment of the present disclosure with a connector connected to the outlet port to a pump as seen from an isometric view.

In yet another embodiment, the inlet port 24 is on the side of the outer wall 12 and is near the end where the outlet port 26 is. In another embodiment, the inlet port 24 is on the side of the outer wall 12 and is in the middle of the outer wall 12 and between the outlet port 26 and the valve 28 as shown in FIG. 11. In yet another embodiment, the inlet port 24 is on the side of the outer wall 12 and is near the end where the valve 28 is. In yet another embodiment, the inlet port 24 is on the same end of the outer wall 12 as the outlet port 26. In yet another embodiment, the inlet port 24 is on the same end of the outer wall 12 as the valve 28.

In yet another embodiment, the inlet port 24 is about 0.20" from the outlet port 26. In another embodiment, the inlet port 24 is about 0.21" from the outlet port 26. In yet another embodiment, the inlet port 24 is about 0.22" from the outlet port 26. In yet another embodiment, the inlet port 24 is about 0.23" from the outlet port 26. In yet another embodiment, the inlet port 24 is about 0.24" from the outlet port 26. In yet another embodiment, the inlet port 24 is about 0.25" from the outlet port 26. In yet another embodiment, the inlet port 24 is about 0.26" from the outlet port 26. In yet another embodiment, the inlet port 24 is about 0.27" from the outlet port 26. In yet another embodiment, the inlet port 24 is about 0.28" from the outlet port 26. In yet another embodiment, the inlet port 24 is about 0.29" from the outlet port 26. In yet another embodiment, the inlet port 24 is about 0.30" from the outlet port 26. In yet another embodiment, the inlet port 24 is about 0.31" from the outlet port 26. In yet another aspect of at least one embodiment, the inlet port 24 is about 0.32" from the outlet port 26. In yet another aspect of at least one embodiment, the inlet port 24 is about 0.33" from the outlet port 26. In yet another aspect of at least one embodiment, the inlet port 24 is about 0.34" from the outlet port 26. In yet another aspect of at least one embodiment, the inlet port 24 is about 0.35" from the outlet port 26. In yet another embodiment, the inlet port 24 is about 0.2" to about 1" from the outlet port 26. In yet another embodiment, the inlet port 24 is about 1" to about 1.5" from the outlet port 26. In yet another embodiment, the inlet port 24 is about 1.5" to about 2" from the outlet port 26.

In yet another aspect of at least one embodiment, the inlet port 24 is encompassed by an outer wall, called the inlet port outer wall 10. In one embodiment, the inlet port outer wall 10 is at least 2 mm thick.

In yet another aspect of at least one embodiment, the outlet port 26 comprises of a material that is safe to use in fluid transport or communication and is constructed using a material including, but not limited to, metal, plastic, glass. In one embodiment, the outlet port 26 is about 0.1" in length. In another embodiment, the outlet port 26 is about 0.2" in length. In yet another embodiment, the outlet port 26 is about 0.3" in length. In yet another embodiment, the outlet port 26 is about 0.4" in length. In yet another embodiment, the outlet port 26 is about 0.5" in length. In yet another embodiment, the outlet port 26 is about 0.6" in length. In one embodiment, the outlet port 26 is on one end of the outer wall 12. In another embodiment, the outlet port 26 is on opposite ends with the valve 28. In yet another embodiment, the outlet port 26 and the valve 28 are aligned along a center axis of the outer wall 12.

In one embodiment, the outlet port 26 is encompassed by an outer wall, called the outlet port outer wall 16. In one embodiment, the outlet port outer wall 16 is about 2 mm thick.

In one embodiment, the valve 28 comprises of a material that is safe to use in fluid transport or communication and is constructed using a material including, but not limited to, metal, plastic, glass. The valve 28 is about 12 mm in length. In one embodiment, the valve 28 comprises of a Luer-activated valve to keep the air or gas trapped within the interior chamber 22 until a needle or other object is inserted into the Luer-activated valve to release the air or gas from the interior chamber 22. In this embodiment, the air or gas egresses from the interior chamber 22 to allow for fluid to ingress into the interior chamber 22. In one embodiment, the valve 28 is on one end of the outer wall 12. In another embodiment, the valve 28 is on opposite ends with the outlet port 26. In yet another embodiment, the valve 28 and the outlet port 26 are aligned along a center axis of the outer wall 12. In another embodiment, the valve is not present. The air collects in the interior chamber 22 until full, at which time the apparatus is removed to expel the air.

In one embodiment, the valve 28 is encompassed by an outer wall, called the valve outer wall 16. In one embodiment, this valve outer wall 28 is about 10 mm thick. In another embodiment, the valve outer wall 28 is about 20 mm thick. In yet another embodiment, the valve outer wall 28 is about 30 mm thick. In yet another embodiment, the valve outer wall 28 is about 40 mm thick.

In one embodiment, the tubing clip 14 comprises of a material that is safe to use in fluid transport or communication and is constructed using a material including, but not limited to, metal, plastic, glass. In one embodiment, the tubing clip 14 is at least 6 mm in wide and at least 4 mm in height. In one embodiment, the tubing clip 14 is attached to the side of the outer wall 12. In another embodiment, the tubing clip 14 is attached to the side of the outer wall 12 and is near the valve 28. In yet another embodiment, the tubing clip 14 is attached to the side of the outer wall 12 and is in the middle of the valve 28 and the outlet port 26. In yet another embodiment, the tubing clip 14 is attached to the side of the outer wall 12 and is on opposite sides with the inlet port 24. In yet another embodiment, the tubing clip 14 is attached to the side of the outer wall 12 and is 45 degrees from the inlet port 24. In yet another embodiment, the tubing clip 14 is attached to the side of the outer wall 12 and is 90 degrees from the inlet port 24. In yet another embodiment, the tubing clip 14 is attached to the side of the outer wall 12 and is 135 degrees from the inlet port 24. In yet another embodiment, the tubing clip 14 is attached to the side of the outer wall 12 and is 180 degrees from the inlet port 24. In yet another embodiment, the tubing clip 14 is absent as shown in FIG. 10. In one embodiment, the tubing clip 14 can hold a tube that is 2 mm in diameter.

In yet another embodiment, the interior chamber 22 holds a volume of approximately 5.6 ml and has a diameter of approximately 0.45" with a length of approximately 2.78". The distance between the inlet port 24 and the outlet port 26 is approximately 0.316". The outer diameter of the outlet port 26 and the inlet port 24 is approximately 0.30" with the interior diameter of the outlet port 26 is approximately 0.166". The inlet port 24 is at an approximate 35 degree angle from the outer wall 12. The outer wall 12 has a diameter of approximately 0.625".

In yet another embodiment, the outlet port 26 of the air removal device is connected to a connector 30 on one end and is connected to a pump 32 on the other end. In an aspect of at least one embodiment contained herein, the connector 30 can attach by other known attachment means over the outlet port outer wall 16 including but not limited to snapping into place over the outlet port outer wall 16. In yet another embodiment, the connector 30 screws into place over the outlet port outer wall 16. In yet another embodiment, the outlet port outer wall 16 slips into the connector 30 and applies pressure to the inner wall of the connector 30 to hold the outlet port outer wall 16 in place. In yet another embodiment, the outlet port outer wall 16 slips over the connector 30 and the connector 30 applies pressure to the inner wall of the outlet port 26 to hold the connection in place.

In yet another embodiment, the connector 30 bends to allows the orientation of the air removal device to remain substantially vertical or horizontal. In yet another embodiment, the connector 30 bends at a distance of approximately one-third the length of the connector 30. In yet another embodiment, the connector 30 bends at a distance of approximately two-thirds the length of the connector 30. In yet another embodiment, the connector 30 is made of a material that makes the connector 30 capable of holding the air removal device in a substantially upright position by itself without the assistance of any other connection or device.

In yet another embodiment, the connector 30 has an angle of approximately 90 degrees between the device the air is being removed from and the air removal device. In yet another embodiment, the connector forms an approximately 60 to 120 degree angle between the device the air is being removed from and the air removal device.

It should be appreciated that the connector 30 shown in FIGS. 16-22 provide various benefits and advantages, including but not limited to allowing the air removal device to be used with and directly connected to a variety of devices without creating excess slack in any line or tubing present, allows for proper orientation of the air removal device regardless of the orientation or positioning of the device to which the air removal device connects to. It should be appreciated that the invention of the present disclosure includes using the air removal device and connector 30 outside or inside the device to which is connects to, or both inside and outside the device to which it connects to provide additional protection and functionality.

The following studies are examples of the present disclosure and are not to be limited to these studies. A person having ordinary skills in the art would understand that the present disclosure could apply to other industries and in other applications and that the studies below and the embodiments described herein should not define or limit the invention in any way.

Study 1

Extensive study and evaluations was done on numerous aspects and different embodiment of the present inventions to confirm that the apparatus worked as intended using different infusion pumps, tubing sets and flow rates and liquids. The purpose of one of the studies was to evaluate the functional performance of the apparatus described herein under normal operating conditions/parameters using a broad range of manufacturer's IV infusion pumps. Testing involved a full range of flow rates, the introduction of a wide range of amounts, frequencies and sizes of air bubbles with a full range of representative fluids including crystalloids and blood. Testing also included the use of gravity fed IV set-ups. The testing was designed to test various worst-case conditions to show compatibility with each of the pumps used and determine if any of the apparatus did not work as intended. This testing protocol was partially chosen because it evaluated virtually all of the conditions/parameters that the device would encounter in most applications no matter the industry or environment (e.g., range of flow rates, viscosity of fluids, resistant pressures, and air bubble sizes, volumes and rates of introduction into the system.)

Device Description/Operational Theory

At setup/priming of the infusion set, the air/fluid chamber is filled with fluid. Once primed, fluid is drawn through the system and passes through the fluid inlet, through the device and out to the pump. As the fluid passes through the fluid inlet, air bubbles separate from the fluid and rise up into the air cylinder. The fluid being pumped then exits the device free of air. In some embodiments, an attachment (e.g., a clip) near the top of the air/fluid chamber is provided. The attachment serves at least two purposes: it affixes the top of the apparatus to the tubing set to ensure the vertical orientation that is recommended for optimum functionality, and it also allows the user to easily manage excess tubing length by looping and attaching or clipping the tubing to the apparatus, also facilitating the proper orientation.

Priming of an apparatus equipped tubing set is accomplished using the same basic process as a non-apparatus set. For tubing sets that include a drip chamber, the apparatus is primed by a few extra squeezes of the drip chamber, which takes approximately 5-7 seconds. For sets that do not include a drip chamber, priming is accomplished by holding the apparatus upside down and allowing gravity to fill the apparatus in the same way the tubing set is normally filled.

Test Equipment and Materials

The following materials and equipment were used during the execution of this study: 3D printed prototypes of the gas removal apparatus.

Pumps: Alaris® 8100 Infusion Pump and PC unit, Alaris® 8110 Syringe Infusion Pump and PC unit, Hospira® Plum A+Infusion Pump, Baxter® Flo-Gard 6201 Infusion Pump, Braun® Vista Basic Infusion Pump, Braun® Infusomat Space Infusion Pump, Smith's® Medical 3500 Syringe Infusion Pump, Sigma® Spectrum Infusion Pump, CADD-Prizm® PCS-II Infusion Pump, Curlin® Medical 4000 CMS Infusion Pump.

Administration Sets (used with corresponding pump): Hospira® Macrobore Extension Sets (for use with syringe pumps), CareFusion® SmartSite Infusion Set 2420-0007, Hospira® Primary IV Plumset 12336-0, Baxter® Clearlink System Solution Set 2C8401s (for Sigma® Spectrum and Flo-Gard 3201), Braun® Vista Basic IV Set V9905, Braun® Infusomat Space Pump IV Set 362032, Curlin® Infusion Pump Administration Set, CADD® Yellow Striped Administration Set 21-7024-24.

Fluids & Miscellaneous: Cardinal® Health Irrigation Delivery Set, one liter, used as IV bag/fluid reservoir, 0.9% saline solution, VWR® catalog number 89370-096, Ringer's solution, lactate buffered, VWR® catalog number AAJ67572-K2, Sheep blood, defibrinated, Quad Five product #610-1000, BD® Monoject 60 ml syringes, for use with the syringe pumps, Various syringes and needles, for injecting air bubbles into the system, Protractor.

Test Setup and Parameters

The different gas removal apparatus tested were spliced into the appropriate corresponding tubing set for each pump. Tubing sizes used in the infusion sets vary in diameter.

Tubing sets such as the Carefusion® SmartSite Infusion Set (used with the Alaris® pumps) are relatively large, having an inner diameter of 0.110". Other sets are much smaller, such as the CADD® Yellow Striped Administration set, which has a tubing ID of 0.040". The testing summarized below shows the apparatus functions in the same manner regardless of tubing size. The individual pump, IV set and apparatus setups are shown below. Each pump/tubing setup and apparatus was tested at multiple pump rates using three fluids. Gravity-only testing was completed using an 18-gauge needle at the patient end of the administration set. Pump rates used for testing were based upon the range of available rates specific to each pump, which vary between manufacturers. All pumps were tested at their maximum rates, as well as medium and slow rates (where applicable). Flow rates are summarized for each pump below. A separate test setup was used to determine the maximum angle from vertical at which the apparatus can function. To introduce air into the lines for testing purposes, a syringe pump was used with a Leur connector via a Y port in the tubing. Air was then injected into the lines.

Acceptance Criteria

Acceptance criteria for the functional tests shall be defined as shown in Table 1.

TABLE 1

Table 1: Acceptance Criteria

| Test | Passing Result | Unfavorable Result |
|---|---|---|
| Visual Verification | Bubbles introduced into the system are observed to be removed. | Bubbles introduced into the system are observed to pass through to the pump and set off alarm. In the case of syringe pumps, bubbles are observed to pass through to the downstream tubing. |
| Pump Air Detector | The pump's built-in air detector does not alarm during the test. | The pump's built-in air detector alarms during the test. |

Not all pumps have an air detector. For those pumps (as well as the gravity-only test), visual verification is the only means of air detection and the sole acceptance criterion. Pumps without air detectors are noted below.

Execution

Preparation for testing and test execution took place at the R&D lab of Innovative Health, Scottsdale, Ariz., which is an ISO 13485 certified and 21 CFR 820 compliant medical device manufacturing facility.

Summary of Results

Refer to Tables 2-13 below for results of each test. Acceptance criteria for all tests were successfully met.

TABLE 2

Table 2: Alaris ® 8100 Pump Test Results - Continued

| Test | Pump Rate (ml/hr) | Visual Verification Result | Air Detector Result |
|---|---|---|---|
| Saline | 999 | PASS | PASS |
| | 500 | PASS | PASS |
| | 200 | PASS | PASS |
| | 125 | PASS | PASS |
| | 75 | PASS | PASS |

TABLE 2-continued

Table 2: Alaris ® 8100 Pump Test Results - Continued

| Test | Pump Rate (ml/hr) | Visual Verification Result | Air Detector Result |
|---|---|---|---|
| | 50 | PASS | PASS |
| | 25 | PASS | PASS |
| | 5 | PASS | PASS |
| Ringer's | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Blood | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |

NOTES:
N/A

TABLE 3

Table 3: Alaris ® 8110 Syringe Pump Test Results - Continued

| Test | Pump Rate (ml/hr) | Visual Verification Result | Air Detector Result |
|---|---|---|---|
| Saline | 999 | PASS | N/A |
| | 500 | PASS | |
| | 200 | PASS | |
| | 125 | PASS | |
| | 75 | PASS | |
| | 50 | PASS | |
| | 25 | PASS | |
| | 5 | PASS | |
| Ringer's | 999 | PASS | |
| | 500 | PASS | |
| | 200 | PASS | |
| | 125 | PASS | |
| | 75 | PASS | |
| | 50 | PASS | |
| | 25 | PASS | |
| | 5 | PASS | |
| Blood | 999 | PASS | |
| | 500 | PASS | |
| | 200 | PASS | |
| | 125 | PASS | |
| | 75 | PASS | |
| | 50 | PASS | |
| | 25 | PASS | |
| | 5 | PASS | |

NOTES:
System is not equipped with an air detector.

TABLE 4

Table 4: Baxter ® Flo-Gard 6201 Pump Test Results - Continued

| Test | Pump Rate (ml/hr) | Visual Verification Result | Air Detector Result |
|---|---|---|---|
| Saline | 1999 | PASS | PASS |
| | 500 | PASS | PASS |
| | 200 | PASS | PASS |
| | 125 | PASS | PASS |
| | 75 | PASS | PASS |
| | 50 | PASS | PASS |

TABLE 4-continued

Table 4: Baxter ® Flo-Gard 6201 Pump Test Results - Continued

| Test | Pump Rate (ml/hr) | Visual Verification Result | Air Detector Result |
|---|---|---|---|
| | 25 | PASS | PASS |
| | 5 | PASS | PASS |
| Ringer's | 1999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Blood | 1999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |

NOTES:
At 1999 ml/hr, this pump's maximum speed is much greater than all other pumps tested during this study.

TABLE 5

Table 5: Hospira ® Plum A + Pump Test Results - Continued

| Test | Pump Rate (ml/hr) | Visual Verification Result | Air Detector Result |
|---|---|---|---|
| Saline | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Ringer's | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Blood | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |

NOTES:
N/A

TABLE 6

Table 6: Braun ® Vista Basic Pump Test Results - Continued

| Test | Pump Rate (ml/hr) | Visual Verification Result | Air Detector Result |
|---|---|---|---|
| Saline | 800 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Ringer's | 800 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Blood | 800 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |

NOTES:
Maximum pump speed is 800 ml/hr.

TABLE 7

Table 7: Braun ® Infusomat Space Pump Test Results - Continued

| Test | Pump Rate (ml/hr) | Visual Verification Result | Air Detector Result |
|---|---|---|---|
| Saline | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Ringer's | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Blood | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |

NOTES:
N/A

TABLE 8

Table 8: Smith's ® Medical 3500 Syringe Pump Test Results - Continued

| Test | Pump Rate (ml/hr) | Visual Verification Result | Air Detector Result |
|---|---|---|---|
| Saline | 944 | PASS | N/A |
| | 500 | PASS | |
| | 200 | PASS | |
| | 125 | PASS | |
| | 75 | PASS | |
| | 50 | PASS | |

TABLE 8-continued

Table 8: Smith's ® Medical 3500 Syringe Pump Test Results - Continued

| Test | Pump Rate (ml/hr) | Visual Verification Result | Air Detector Result |
|---|---|---|---|
| | 25 | PASS | |
| | 5 | PASS | |
| Ringer's | 944 | PASS | |
| | 500 | PASS | |
| | 200 | PASS | |
| | 125 | PASS | |
| | 75 | PASS | |
| | 50 | PASS | |
| | 25 | PASS | |
| | 5 | PASS | |
| Blood | 944 | PASS | |
| | 500 | PASS | |
| | 200 | PASS | |
| | 125 | PASS | |
| | 75 | PASS | |
| | 50 | PASS | |
| | 25 | PASS | |
| | 5 | PASS | |

NOTES:
Maximum pump speed is 944 ml/hr. System is not equipped with an air detector.

TABLE 9

Table 9: CADD ® Prizm Pump Test Results - Continued

| Test | Pump Rate (ml/hr) | Visual Verification Result | Air Detector Result |
|---|---|---|---|
| Saline | 347 | PASS | N/A |
| | 30 | PASS | |
| | 25 | PASS | |
| | 5 | PASS | |
| Ringer's | 347 | PASS | |
| | 30 | PASS | |
| | 25 | PASS | |
| | 5 | PASS | |
| Blood | 347 | PASS | |
| | 30 | PASS | |
| | 25 | PASS | |
| | 5 | PASS | |

NOTES:
Maximum pump speed is 347 ml/hr using "Prime" function. Maximum speed in "Continuous" mode is 30 ml/hr. System is not equipped with an air detector.

TABLE 10

Table 10: Curlin ® Medical 4000 CMS Pump Test Results - Continued

| Test | Pump Rate (ml/hr) | Visual Verification Result | Air Detector Result |
|---|---|---|---|
| Saline | 400 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Ringer's | 400 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Blood | 400 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |

NOTES:
Maximum pump speed is 400 ml/hr.

TABLE 11

Table 11: Sigma ® Spectrum Pump Test Results - Continued

| Test | Pump Rate (ml/hr) | Visual Verification Result | Air Detector Result |
|---|---|---|---|
| Saline | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Ringer's | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |
| Blood | 999 | PASS | PASS |
| | 500 | PASS | PASS |
| | 200 | PASS | PASS |
| | 125 | PASS | PASS |
| | 75 | PASS | PASS |
| | 50 | PASS | PASS |
| | 25 | PASS | PASS |
| | 5 | PASS | PASS |

NOTES:
N/A

TABLE 12

Table 12: Gravity Test Results

| Test | Visual Verification Result |
|---|---|
| 18-gauge needle, saline | PASS |
| 18-gauge needle, blood | PASS |

NOTES:
N/A

TABLE 13

Table 13: Orientation Assessment

| Test | Result |
|---|---|
| Angle determination | The device is capable of full functionality at 14 degrees from horizontal (76 degrees from vertical). |

NOTES:
Testing performed using saline; Baxter ® 6201 pump at maximum speed (1999 ml/hr).

CONCLUSION

Based on the results of the above tests, the acceptance criteria for each pump were successfully met. The test results demonstrate gas removal apparatus tested function as intended when used with each pump tested as well as when used in a gravity-only system. The apparatus tested worked at slow pump/gravity speeds (as low as 30 ml/hr) as well as the maximum rate of the fastest pump provided for testing (1999 ml/hr) using thin fluids (0.9% saline) and relatively viscous fluids (blood).

The testing performed during the execution of this study shows that the gas removal apparatus effectively removes air bubbles at angles as low as 14 degrees from the horizontal position.

The test results also indicate the gas removal apparatus will function as intended with chemotherapy drugs.

Study 2

Additional testing was performed to help determine the ideal size for the apparatus.

This version of the device was been scaled down to a smaller overall package while maintaining dimensions critical to air removal. Tubing clip functionality was maintained by rotating the clip 90 degrees from the inlet port.

Test Setup and Parameters

The Baxter® 6201 pump was used due to its maximum flow rate (1999 ml/hr) being double the rate (or more) of most other pumps. High flow rates have been shown to be the worst-case challenge to the apparatus.

The device was tested at multiple pump rates using saline and bubbles ranging in size and frequency.

Acceptance Criteria

Acceptance criteria for the smaller/lower capacity tests shall be defined as shown in Table 1.

Execution

Testing of the smaller/lower capacity apparatus took place during the week of Apr. 23, 2018 at the R&D lab of Innovative Health, Scottsdale, Ariz., which is an ISO 13485 certified and 21 CFR 820 compliant medical device manufacturing facility.

Summary of Results

Refer to Table 14 for results of each air removal test. Acceptance criteria for all tests were successfully met.

TABLE 14

Table 14: Smaller/Lower Capacity Apparatus Test Results

| Test | Pump Rate (ml/hr) | Visual Verification Result | Air Detector Result |
|---|---|---|---|
| Saline | 1999 | PASS | PASS |
|  | 500 | PASS | PASS |
|  | 200 | PASS | PASS |

Summary of Smaller/Lower Capacity Apparatus Testing

Testing performed during this evaluation shows that a smaller version of the apparatus functions in a manner equivalent to the larger versions. The smaller apparatus has no impact on the device's ability to remove air.

This version has a 1.8 ml capacity. This version is likely the most preferable design for the following reasons:

During a 56-hour evaluation, the maximum amount of air captured was approximately 1 ml, which shows the 1.8 ml version of the device has sufficient capacity.

The 1.8 ml capacity of this design is approximately 40% of the volume of the upstream tubing of a typical tube set. If air fills nearly half of the upstream tubing, there is likely a more serious condition that needs to be addressed (e.g., empty IV bag).

The smaller size integrates more easily into existing packaging and adds less bulk and weight to the tubing set.

The smaller size is much less likely to tilt/lean away from the approximately vertical orientation that is recommended for optimal functioning.

Study 3

Additional testing was performed to determine the ability of the apparatus to remove air when placed in the downstream tubing.

Test Setup and Parameters

The Baxter® 6201 pump was used due to its maximum flow rate (1999 ml/hr) being double the rate (or more) of most other pumps. High flow rates have been shown to be the worst-case challenge to the apparatus.

An apparatus was spliced into the downstream segment of the tubing set between the Y-port and the patient end of the set.

The device was tested at multiple pump rates using saline and bubbles ranging in size and frequency.

Acceptance Criteria

Acceptance criteria for the downstream tests shall be defined as shown in Table 1.

Execution

Testing of the downstream apparatus took place during the week of Apr. 30, 2018 at the R&D lab of Innovative Health, Scottsdale, Ariz., which is an ISO 13485 certified and 21 CFR 820 compliant medical device manufacturing facility.

Summary of Downstream Apparatus Test Results

Refer to Table 15 for results of each air removal test. Acceptance criteria for all tests were successfully met.

TABLE 15

Table 15: Downstream Apparatus Air Removal Test Results

| Test | Pump Rate (ml/hr) | Visual Verification Result | Air Detector Result |
|---|---|---|---|
| Saline | 1999 | PASS | PASS |
|  | 500 | PASS | PASS |
|  | 200 | PASS | PASS |

Study 4

Additional testing was performed to evaluate the performance of the apparatus at very low pump speed (5-10 ml/hr)

Test Setup and Parameters

The Braun® Vista Basic pump and tubing set were used with a 6 ml injection-molded apparatus for this testing.

The device was tested at two pump rates using saline and bubbles ranging in size and frequency.

Acceptance Criteria

Acceptance criteria for the low speed tests shall be defined as shown in Table 1.

Execution

Testing of the low speed apparatus took place during the week of May 16, 2018 at the R&D lab of Innovative Health, Scottsdale, Ariz., which is an ISO 13485 certified and 21 CFR 820 compliant medical device manufacturing facility.

Summary of Low Pump Speed Test Results

Refer to Table 16 for results of each air removal test. Acceptance criteria for all tests were successfully met.

TABLE 16

Table 16: Low Pump Speed Air Removal Test Results

| Test | Visual Verification Result | Air Detector Result |
|---|---|---|
| 5 ml/hr with saline | PASS | PASS |
| 10 ml/hr with saline | PASS | PASS |

Study 5

During this evaluation it was noted that the Alaris® 8100 tube set/pump combination is prone to developing air bubbles in the segment of tubing that passes through/engages with the pump mechanism.

This condition was observed to some extent in other pumps used during apparatus evaluations. However, the Alaris® 8100 was the only pump that would develop enough air in this manner to trigger the alarm, which was only minimally mitigated by the use of the downstream apparatus (appropriately 20% reduction).

The severity of this condition in the Alaris® 8100 pump could be attributed to its design features. Compared to other tubing sets, the Alaris® 8100 set has a softer (likely silicone) segment of tubing that integrates with the pump mechanism. It also has an additional joint/disruption in the tubing caused by the inline safety clamp. These features may contribute to the formation of air.

Air was also observed in the downstream tubing directly beneath the pump housing. It is unclear if this air formed in this area or came from above.

In an effort to reduce the frequency of alarms caused by this air formation, a second apparatus was spliced into the tubing set, placed directly below the pump.

The efficacy of the downstream apparatus was evaluated by running two pump/tubing setups side-by-side to compare alarm frequency. One setup was equipped with apparatus devices upstream and downstream. The second setup used an unaltered tube set.

The upstream apparatus was used to ensure that any alarms were not caused by air coming from the upstream section of tubing.

The results of this evaluation are summarized in Table 17.

The air noted above was observed to be captured in the downstream apparatus as it moved with the fluid flow. No additional bubbles were observed in the tubing below the downstream apparatus.

TABLE 17

Table 17: Downstream Apparatus Results

| | Number of Alarms During Test | |
|---|---|---|
| Test Duration | Alaris® 8100 with Apparatus | Alaris® 8100 without Apparatus |
| 56 Hours | 4 | 4 |

Summary of Results of the Downstream Testing With Alaris® 8100

The testing performed in this study indicates that when the apparatus is used on the downstream side of the pump, the apparatus can reduce alarms by 20%.

The testing performed in this study also indicates that the apparatus prevents air in the downstream tubing from reaching the patient.

Study 6

The purpose of this study is to evaluate the performance of the gas removal apparatus with Luer-Activated Valve.

Device Description/Operational Theory

At setup/priming of the infusion set, the air/fluid chamber is filled with fluid. Once primed, fluid is drawn through the system and passes through the fluid inlet, through the device and out to the pump. As the fluid passes through the fluid inlet, air bubbles separate from the fluid and rise up into the air cylinder. The fluid being pumped then exits the device free of air. A clip feature near the top of the air/fluid chamber serves two purposes: it affixes the top of the device to the tubing set to ensure the vertical orientation that is recommended for optimum functionality, and it also allows the user to easily manage excess tubing length by looping and clipping the tubing to the device, also facilitating the proper orientation.

This version of the device incorporates a Luer-activated valve located at the top of the air/fluid chamber and allows for the evacuation of extracted air and simultaneous refilling of the chamber with fluid. This valve also facilitates easier priming of the tubing set/apparatus when the apparatus is used in a tubing set that does not include a drip chamber.

Test Equipment and Materials

The following materials and equipment were used during the execution of this evaluation: Baxter® Flo-Gard 6201 Infusion Pump, 0.9% saline solution, VWR® catalog number 89370-096, gas removal apparatus, 3D printed prototype, with Luer-Activated Valve, Innovative Therapies® Irrigation Delivery Set, one liter, used as IV bag.

Test Setup and Parameters

The pump, IV set and apparatus test setup. The Baxter® 6201 pump was used due to its maximum flow (1999 ml/hr)

rate being double that of most other pumps. High flow rates have been shown to be the worst-case challenge to the apparatus. The device was tested at multiple pump rates using saline and bubbles ranging in size and frequency. Refer to Table 1 for test conditions and results.

Eexecution

Preparation for testing and test execution took place during the week of Feb. 20, 2018 at the R&D lab of Innovative Health, Scottsdale, Ariz., which is an ISO 13485 certified and 21 CFR 820 compliant medical device manufacturing facility.

Summary of Results

Refer to Table 18 for results of each air removal test. Refer below for a summary of the air evacuation/chamber refilling test. Acceptance criteria for all tests were successfully met.

TABLE 18

Table 18: Air Removal Test Results

| Test | Pump Rate | Visual Verification Result | Air Detector Result |
|---|---|---|---|
| High speed with saline | 1999 ml/hr | PASS | PASS |
| Medium speed with saline | 500 ml/hr | PASS | PASS |
| Low speed with saline | 200 ml/hr | PASS | PASS |

Air Evacuation/Fluid Refilling Evacuation

As part of this evaluation, air was introduced into the tubing set and captured by the apparatus to the device's maximum capacity. At that point the pump was paused. A standard 10 ml syringe was attached to the Luer-activated valve. Upon plunger retraction, air was removed from the chamber. Simultaneously, fluid was drawn into the chamber from the upstream tubing, refilling the chamber.

The testing performed during this evaluation shows the Luer-activated valve feature works as intended.

CONCLUSION

Testing performed during this evaluation shows that this version of the apparatus functions in a manner equivalent to the non-valved version. The addition of the valve has no impact on the device's ability to remove air. Since the valve is closed until a syringe is attached, the air chamber is still a closed vessel during operation. This evaluation also shows that when needed, the Luer-activated valve effectively serves its purpose of refilling the chamber with fluid/ removing captured air.

What is claimed is:

1. An apparatus consisting of:
   an outer wall, wherein the outer wall encompasses an interior chamber;
   an interior chamber, wherein the interior chamber holds a predetermined volume of fluid and gas;
   an inlet port, wherein the inlet port allows for fluid to ingress into the interior chamber, and;
   an outlet port, wherein the outlet port allows for fluid to egress out of the interior chamber; and
   a connector, wherein the connector connects to the outlet port to allow for fluid communication between the outlet port and a pump;
   wherein the inlet port is at an angle that is less than perpendicular and greater than parallel to the outer wall, and is located at a distance that is closer to the bottom outer wall of the chamber than the top outer wall of the chamber.

2. The apparatus of claim 1, wherein the inlet port and the outlet port are at a minimum of 0.25" distance from each other.

3. The apparatus of claim 1, wherein the predetermined volume is a minimum of 1.0 ml of fluid.

4. The apparatus of claim 1, wherein the diameter of the interior chamber is a minimum of 0.35".

5. The apparatus of claim 1, wherein the inlet port is adapted so that a tube can be connected to the inlet port such that fluid flowing through the inlet port enters the interior chamber.

6. The apparatus of claim 1, wherein the apparatus is oriented at least 14 degrees from the horizontal plane.

7. The apparatus of claim 1, wherein the outlet port and the inlet port are on opposite ends of the outer wall and aligned along a center axis.

8. An apparatus consisting of:
   an outer wall, wherein the outer wall encompasses an interior chamber, and wherein the outer wall has two flat ends;
   an interior chamber that can hold a minimum volume of 1.0 ml;
   an inlet port, wherein the inlet port is attached to the outer wall at an angle from the outer wall;
   an outlet port on one end of the outer wall; wherein the outlet port and the inlet port are at a minimum of 0.25" mm distance from each other;
   a valve on the opposite end of the outer wall as the outlet port; and
   a connector, wherein the connector connects to the outlet port to allow for fluid communication between the outlet port and a pump;
   wherein the inlet port is located at a distance that is closer to the bottom outer wall of the chamber than the top outer wall of the chamber.

9. The apparatus of claim 8, wherein the inlet port is adapted so that a tube can be connected to the inlet port such that fluid flowing through the inlet port enters the interior chamber.

10. The apparatus of claim 8, wherein the inlet port is at an angle that is greater than 10 degrees but less than or equal to 90 degrees to the outer wall.

11. The apparatus of claim 8, wherein the valve is a Luer-activated valve and wherein the valve is closed to trap air or gas inside the interior chamber.

12. The apparatus of claim 8, wherein the apparatus is oriented at least 14 degrees from the horizontal plane.

13. An apparatus consisting of:
   an outer wall, wherein the outer wall encompasses an interior chamber;
   an interior chamber that can hold a minimum volume of 1.0 ml;
   an inlet port, wherein the inlet port is attached to the outer wall at a degree that is less than perpendicular and greater than parallel to the outer wall;

an outlet port on one end of the outer wall, wherein the outlet port and the inlet port are at a minimum of 0.25" mm distance from each other;

a valve on the opposite end of the outer wall as the outlet port, wherein the valve and the outlet port are on opposite ends of the outer wall and are aligned along a center axis, and wherein the valve is closed to trap air or gas inside the interior chamber;

and a connector, wherein the connector connects to the outlet port to allow for fluid communication between the outlet port and a pump and the inlet port is located at a distance that is closer to the bottom outer wall of the chamber than the top outer wall of the chamber.

14. The apparatus of claim 13, wherein the valve is a Luer-activated valve.

15. The apparatus of claim 13, wherein an object is inserted into the valve to remove the air or gas from the interior chamber and to allow for more liquid to ingress into the interior chamber through the inlet port.

16. The apparatus of claim 13, wherein the apparatus is oriented at least 14 degrees from the horizontal plane.

\* \* \* \* \*